(12) United States Patent
Shaw et al.

(10) Patent No.: US 7,595,300 B2
(45) Date of Patent: Sep. 29, 2009

(54) 7-QUINOLYL KETOLIDE ANTIBACTERIAL AGENTS

(75) Inventors: Simon James Shaw, San Francisco, CA (US); Gary W Ashley, Alameda, CA (US); Mark A. Burlingame, Oakland, CA (US)

(73) Assignee: Kosan Biosciences Incorporated, Princeton, NJ (US)

( * ) Notice: Subject to any disclaimer, the term of this patent is extended or adjusted under 35 U.S.C. 154(b) by 361 days.

(21) Appl. No.: 11/636,206

(22) Filed: Dec. 7, 2006

(65) Prior Publication Data

US 2008/0096828 A1    Apr. 24, 2008

Related U.S. Application Data

(60) Provisional application No. 60/750,489, filed on Dec. 13, 2005.

(51) Int. Cl.
*A61K 31/70* (2006.01)
*C07H 17/08* (2006.01)

(52) U.S. Cl. .......................... 514/29; 536/7.4
(58) Field of Classification Search .................. 536/7.4
See application file for complete search history.

(56) References Cited

U.S. PATENT DOCUMENTS

| | | | |
|---|---|---|---|
| 5,274,085 A | 12/1993 | Amano | |
| 5,635,485 A | 6/1997 | Agouridas | |
| 5,719,272 A | 2/1998 | Yang | |
| 5,750,510 A | 5/1998 | Elliott | |
| 5,808,017 A | 9/1998 | Chang | |
| 5,852,180 A | 12/1998 | Patel | |
| 5,866,549 A | 2/1999 | Or | |
| 6,124,269 A | 9/2000 | Phan | |
| 6,395,710 B1 | 5/2002 | Chu | |
| 6,399,582 B1 | 6/2002 | Hlasta | |
| 6,417,366 B2 | 7/2002 | Allen | |
| 6,437,106 B1 | 8/2002 | Stoner | |
| 6,451,768 B1 | 9/2002 | Chu | |
| 6,455,608 B1 | 9/2002 | Jia | |
| 6,458,771 B1 | 10/2002 | Hlasta | |
| 6,492,562 B1 | 12/2002 | Ashley | |
| 6,514,944 B2 | 2/2003 | Chu | |
| 6,579,986 B2 | 6/2003 | Allen | |
| 6,590,083 B1 | 7/2003 | Hlasta | |
| 6,593,302 B2 | 7/2003 | Chu | |
| 6,762,168 B2 | 7/2004 | Chu | |
| 6,794,366 B2 | 9/2004 | Chu | |

2003/0125531 A1    7/2003   Zhang

OTHER PUBLICATIONS

H. Ohtani et al., "Comparative pharmacodynamic analysis of Q-T interval prolongation induced by macrolides clarithromycin, roxithromycin, and azithromycin in rats," *Antimicrobial Agents Chemther.* 44: 2630-2637 (2000).
D.J. Plata et al., "The synthesis of ketolide antibiotic ABT-773 (cethromycin)," *Tetrahedron* 60: 10171-10180 (2004).
E.J. Stoner et al., "Allylation of erythromycin derivatives: introduction of allyl substituents into highly hindered alcohols," *J. Org. Chem.* 68: 8847-8852.
Y.S. Or et al., "Design, synthesis, and antimicrobial activity of 6-O-substituted ketolides active against resistant respiratory tract pathogens," *J.Med. Chem.* 43: 1045-1049.
R.E. Clark et al., "Synthesis and antibacterial activity of novel 6-O-substituted erythromycin A derivatives," *Bioorg. Med. Chem. Letts.* 10: 815-819 (2000).
C. Agouridas et al., "Synthesis and antibacterial activity of ketolides (6-O-methyl-3-oxoerythromycin derivatives): a new class of antibacterials highly potent against macrolide-resistant and -suspectible respiratory pathogens," *J.Med.Chem.* 41: 4080-4100.
Z. Ma et al., "Novel erythromycin derivatives with aryl groups tethered to the C-6 position are potent protein synthesis inhibitors and active against multidrug-resistant respiratory pathogens," *J. Med. Chem.* 44: 4137-4156 (2001).

*Primary Examiner*—Elli Peselev
(74) *Attorney, Agent, or Firm*—Anastasia P. Winslow; Elliott Korsen

(57) ABSTRACT

15-fluoroketolides of the formula

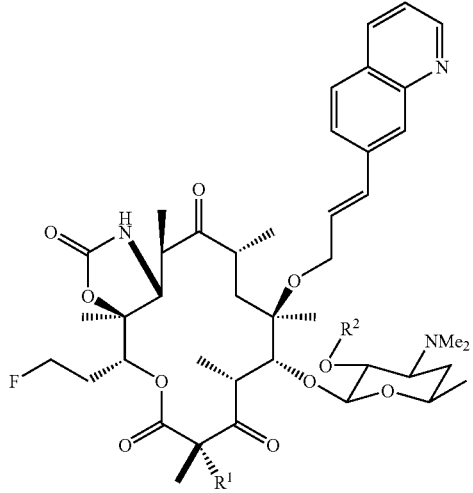

having improved activity and safety, compositions comprising them, and methods for their preparation and use in the treatment of bacterial infections.

23 Claims, 9 Drawing Sheets

A.

B.

A.

B.

A.

B.

7-QUINOLYL KETOLIDE ANTIBACTERIAL AGENTS

CROSS-REFERENCE TO RELATED APPLICATIONS

This application claims priority under 35 U.S.C. §119(e) to U.S. Provisional Application Ser. No. 60/750,489, filed Dec. 13, 2005, which is incorporated herein in its entirety by reference.

STATEMENT OF GOVERNMENT INTEREST

This invention was made in whole or in part with governmental support from National Institute of Allergy and Infectious Disease under SBIR grant No. 5R44 AI051106. Accordingly, the government may have certain rights in the invention.

TECHNICAL FIELD

The invention is directed to antibacterial compounds that expand the repertoire of erythromycin-like antibiotics. More particularly, the invention concerns ketolide antibiotics containing a modified erythronolide nucleus.

BACKGROUND

An increasing number of microbial strains have acquired resistance to the currently available antibiotic compounds, resulting in a potentially dangerous threat to public health. Thus the need for expanding the options available to treat microbial-based conditions has grown with the increasing use of antibiotics. The need for new antimicrobial compounds extends beyond treatment of human and animal infections to a need to preserve food and other perishable commodities. New antibiotics can also be essential for treatment of plants having microbial infections and to the preservation of materials that otherwise are subject to microbially caused corrosion. Thus, there is a clear need for an expanded armament of compounds which can provide a multifaceted defense against unwanted microbial activity.

U.S. Pat. No. 5,866,549 (which is incorporated herein by reference) and U.S. Pat. No. 5,635,485 disclose modified forms of erythromycin which lack a cladinose residue at the 3-position and which are derivatized in various ways in positions 9-12 of the macrolide ring. Such erythromycin derivatives lacking the cladinose and having a 3-keto group are termed "ketolides." U.S. Pat. No. 5,750,510 (incorporated herein by reference) also discloses modified erythromycin derivatives. All of the compounds disclosed in the above-referenced patent documents are derived from erythromycin A, and thus contain an ethyl group at position 13 of the macrolide ring.

While erythromycin A and its chemical derivatives have found long-standing use in the treatment of microbial diseases, it has recently been discovered that these antibacterials have significant safety risks associated with their use. In particular, these antibacterials have been shown to inhibit certain ion channels in cardiac tissues resulting in lengthening of the QT interval in the electrocardiogram. Such lengthening of the QT interval is associated with induction of torsades de pointes in susceptible individuals, occasionally leading to cardiac arrest. See, for example, H. Ohtani et al., "Comparative pharmacodynamic analysis of Q-T interval prolongation induced by the macrolides clarithromycin, roxithromycin, and azithromycin in rats," *Antimicrobial Agents & Chemotherapy* (2000) 44: 2630-2637. The principal cardiac ion channel thought to be involved in this, the hERG or $I_{rK}$ channel, is inhibited by a wide range of drugs with no clear structure-activity relationship, precluding prediction of intrinsic binding affinities of drugs to the channel. Further, hERG is a membrane-spanning ion channel with extracellular and cytosolic faces, and inhibition of hERG by erythromycin-like antibacterials is believed to occur by binding of the drug to the cytosolic face of the channel. As erythromycin-like antibiotics are often actively accumulated into cells at unpredictable levels, the effects of particular macrolide antibacterials on the QT interval are extremely complex and impossible to predict based on their structure.

There thus exists a need for new antibacterial agents having improved efficacy and cardiac safety. U.S. Pat. No. 6,395,710 (incorporated herein by reference) discloses ketolide antiinfective agents prepared from analogs of erythromycin A, which are in turn prepared by genetic engineering. These ketolides show improved activity against a range of erythromycin-sensitive and resistant microorganisms. After extensive testing, we have unexpectedly discovered particular combinations of substituents on these compounds that provide not only improved antibacterial activity but also improved pharmacokinetic behavior and cardiac safety. Such compounds are of particular importance for the safe, effective treatment of bacterial infections.

SUMMARY OF THE INVENTION

In one aspect, the invention relates to particular macrolide antiinfective agents having improved safety and efficacy.

In one embodiment of the invention, 7-quinolyl ketolide compounds having the general structure (I) and pharmaceutically acceptable salts thereof are provided

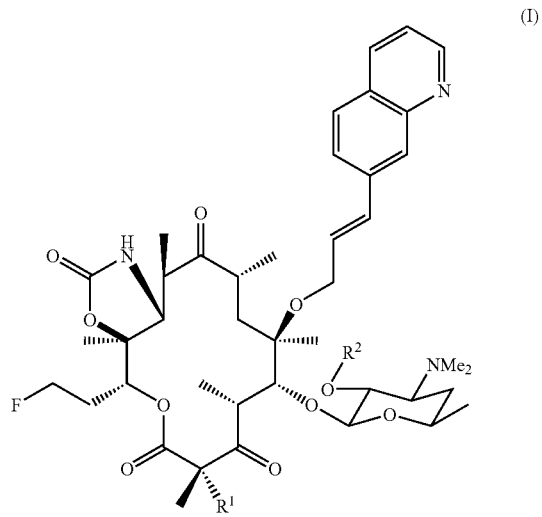

wherein $R^1$ is H or F and $R^2$ is H or a hydroxyl protecting group. In a particular embodiment of the invention, compounds of formula (I) and pharmaceutically acceptable salts thereof wherein $R^1$ is H or F and $R^2$ is H or $R^3CO$, wherein $R^3$ is substituted or unsubstituted $C_1$-$C_5$ alkyl, substituted or unsubstituted aryl, or substituted or unsubstituted heteroaryl are provided.

In one embodiment of the invention, compounds of formula (I) are provided wherein $R^1$ is H. In one particular embodiment of the invention, compounds of formula (I) and pharmaceutically acceptable salts thereof wherein $R^1$ is H and $R^2$ is H or $R^3CO$, wherein $R^3$ is substituted or unsubstituted $C_1$-$C_5$ alkyl or substituted or unsubstituted aryl, are provided. In a more particular embodiment, compounds of formula (I) and pharmaceutically acceptable salts thereof wherein $R^1$ is H and $R^2$ is H or $R^3CO$, wherein $R^3$ is $CH_3$, $CH_3CH_2$, $CH_3CH_2O(C=O)CH_2CH_2$, or phenyl are provided.

In one embodiment of the invention, compounds of formula (I) are provided wherein $R^1$ is F. In one particular embodiment of the invention, compounds of formula (I) and pharmaceutically acceptable salts thereof wherein $R^1$ is F and $R^2$ is H or $R^3CO$, wherein $R^3$ is substituted or unsubstituted $C_1$-$C_5$ alkyl or substituted or unsubstituted aryl, are provided. In a more particular embodiment, compounds of formula (I) and pharmaceutically acceptable salts thereof wherein $R^1$ is F and $R^2$ is H or $R^3CO$, wherein $R^3$ is $CH_3$, $CH_3CH_2$, $CH_3CH_2O(C=O)CH_2CH_2$, or phenyl are provided.

In more particular embodiments of the invention, compounds of formula (II) and (III) and pharmaceutically acceptable salts thereof are provided.

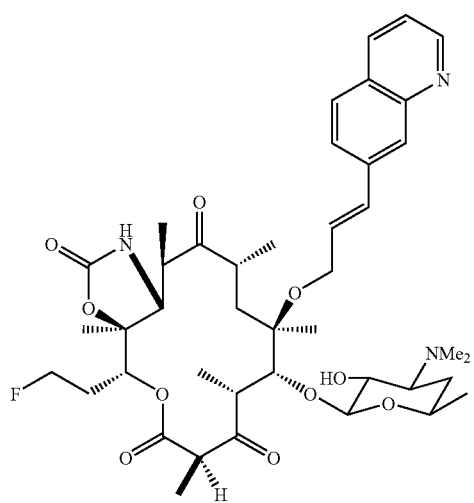

(II)

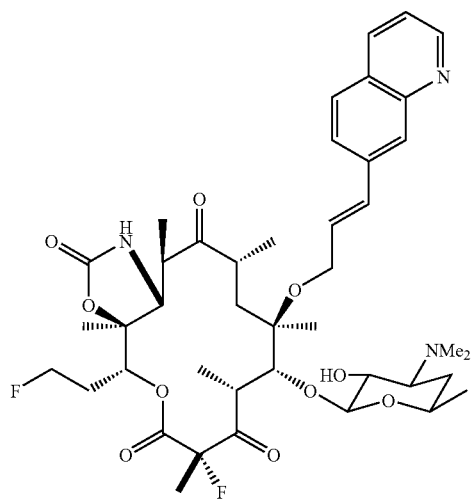

(III)

In another aspect of the invention, methods for the preparation of the compounds of formula (I) and intermediates thereto are provided. In one embodiment of the invention, a method is provided for preparing a compound of formula (IV), an intermediate for the preparation of compounds of formula (I),

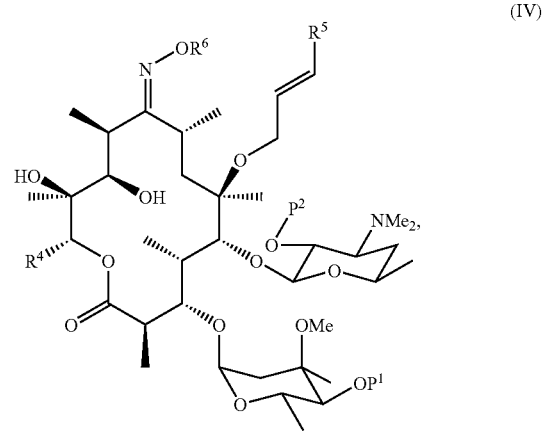

(IV)

wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $R^5$ is H, unsubstituted or substituted heteroaryl, or unsubstituted or substituted aryl; $P^1$ and $P^2$ are each independently hydroxyl protecting groups; and $R^6$ is a hydroxyl protecting group; the method comprising the step of reacting a compound of formula (V)

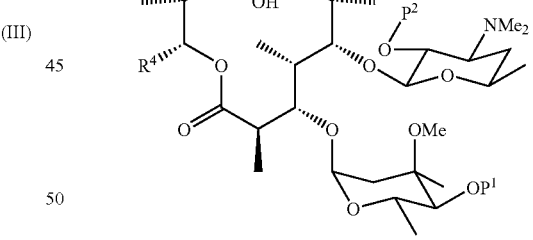

(V)

wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $P^1$ and $P^2$ are each independently hydroxyl protecting groups; and $R^6$ is a hydroxyl protecting group; with a compound of formula (VIa), (VIb), or (VIc)

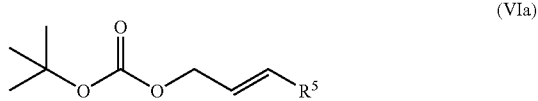

(VIa)

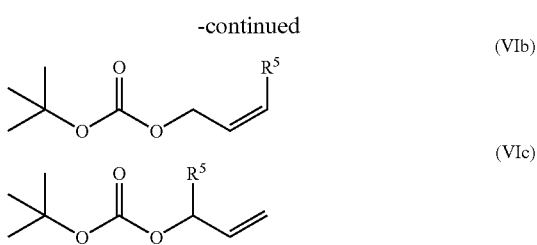

wherein R⁵ is H, unsubstituted or substituted heteroaryl, or unsubstituted or substituted aryl; in the presence of a metal catalyst not having a phosphine ligand.

In a particular embodiment of the invention, a method of preparing compounds of formula (IV), wherein R⁴ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; R⁵ is H, unsubstituted or substituted heteroaryl, or unsubstituted or substituted aryl; P¹ and P² are each independently hydroxyl protecting groups; and R⁶ is a hydroxyl protecting group is provided wherein the metal catalyst comprises palladium in the presence of an isocyanide ligand.

In a more particular embodiment of the invention, a method of preparing compounds of formula (IV), wherein R⁴ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; R⁵ is H, unsubstituted or substituted heteroaryl, or unsubstituted or substituted aryl; P¹ and P² are each independently hydroxyl protecting groups, and R⁶ is a hydroxyl protecting group is provided, wherein the metal catalyst comprises palladium in the presence of tert-butylisocyanide.

In a more particular embodiment of the invention, a method is provided for preparing compounds of formula (IV), wherein R⁴ is unsubstituted or substituted $C_1$-$C_8$ alkyl; R⁵ is H, unsubstituted or substituted heteroaryl, or unsubstituted or substituted aryl; P¹ and P² are each independently hydroxyl protecting groups; and R⁶ is a hydroxyl protecting group, wherein the metal catalyst comprises palladium having tert-butylisocyanide as a ligand.

In a more particular embodiment of the invention, a method is provided for preparing compounds of formula (IV), wherein R⁴ is unsubstituted or substituted $C_1$-$C_8$ alkyl; R⁵ is H; P¹ and P² are each independently hydroxyl protecting groups; and R⁶ is a hydroxyl protecting group is provided, wherein the metal catalyst comprises palladium having tert-butylisocyanide as a ligand.

In a more particular embodiment of the invention, a method of preparing compounds of formula (IV), wherein R⁴ is $CH_2CH_2F$; R⁵ is H; and P¹, P², and R⁶ are each benzoyl, and the metal catalyst comprises palladium and tert-butylisocyanide is provided.

In another aspect of the invention, pharmaceutical compositions comprising one or more of the compounds of formula (I) or pharmaceutically acceptable salts thereof are provided. Such pharmaceutical compositions include solid, liquid, lotion, gel, crème, foam, suspension, ointment, and other compositions suitable for parenteral, oral, inhalation, or topical administration.

In one embodiment of the invention, a pharmaceutical composition comprising a compound of formula (II) or formula (III) or pharmaceutically acceptable salts thereof together with a pharmaceutically acceptable carrier is provided. Such pharmaceutical compositions include solid, liquid, lotion, gel, crème, foam, suspension, ointment, and other compositions suitable for parenteral, oral, inhalation, or topical administration.

In another embodiment of the invention, pharmaceutical compositions comprising one or more of the compounds of formula (I) or pharmaceutically acceptable salts thereof are provided wherein the pharmaceutical composition is a solution, gel, crème, suspension, lotion, foam, or ointment suitable for topical application. In a more particular embodiment of the invention, such topical compositions comprise compound (II) or compound (III) or pharmaceutically acceptable salts thereof. In a more particular embodiment of the invention, such topical compositions comprise one or more of the compounds of formula (I) or pharmaceutically acceptable salts thereof at a concentration of 0.05 to 5% w/w. In a more particular embodiment of the invention, such topical compositions comprise compound (II) or compound (III) or pharmaceutically acceptable salts thereof at a concentration of 0.05 to 5% w/w.

In another embodiment of the invention, pharmaceutical compositions comprising one or more of the compounds of formula (I) or pharmaceutically acceptable salts thereof are provided wherein the pharmaceutical composition is a liquid or solid form suitable for oral or parenteral administration.

In another aspect of the invention, methods for the use of compounds of formula (I) or pharmaceutically acceptable salts thereof and pharmaceutical compositions comprising the compounds of formula (I) or pharmaceutically acceptable salts thereof in the treatment of infectious diseases are provided. In one embodiment of the invention, methods to treat pulmonary bacterial infections are provided. In more particular embodiments, the pulmonary infection is selected from a group consisting of pneumonia, bronchitis, tonsillitis, and pharyngitis. In another embodiment of the invention, methods to treat skin infections are provided. In more particular embodiments, the skin infection is acne.

In another aspect of the invention, compounds of formula (I) or pharmaceutically acceptable salts thereof are provided for the preparation of medicaments for the treatment of bacterial infections. In particular embodiments of the invention, compounds of formula (II) and formula (III) or pharmaceutically acceptable salts thereof are provided for the preparation of medicaments for the treatment of bacterial infections.

BRIEF DESCRIPTION OF THE DRAWINGS

FIG. 1A shows one method for the conversion of 15-fluoroerythromycin A (1) into 6-O-allyl-2',4'',9-O-(tribenzoyl)-15-fluoroerythromycin A 9-oxime (4). FIG. 1B shows one method for the conversion of (4) into 6-O-allyl-2',4''-di-O-benzoyl-15-fluoroerythromycin A 11,12-cyclic carbamate (7). FIG. 1C shows one method for the conversion of (7) into a compound of formula (I) wherein X is H and R¹ is PhCO (10). FIG. 1D shows certain methods for the conversion of compounds of formula (I) wherein R¹ is H and R² is PhCO (10) into compounds of formula (I) wherein R¹ is H and R² is H (compound II) and compounds of formula (I) wherein R¹ is F and R² is PhCO (11) or H (compound III).

FIG. 2A shows the effects of a comparator compound of formula (VIII) wherein Z is 6-quinolyl and R⁸ is H. FIG. 2B shows the effects of a comparator compound of formula (VIII) wherein Z is 1,5-naphthyrid-3-yl and R⁸ is H.

FIG. 3A shows the effects of a comparator compound of formula (VIII) wherein Z is 3-quinolyl and $R^8$ is H. FIG. 3B shows the effects of a comparator compound of formula (VIII) wherein Z is 3-quinolyl and $R^8$ is F.

FIG. 4A shows the effects of a comparator compound of formula (VIII) wherein Z is 6-quinoxalyl and $R^8$ is H. FIG. 4B shows the effects of the compound of the invention having formula (II).

DETAILED DESCRIPTION OF THE INVENTION

Figure 1A:
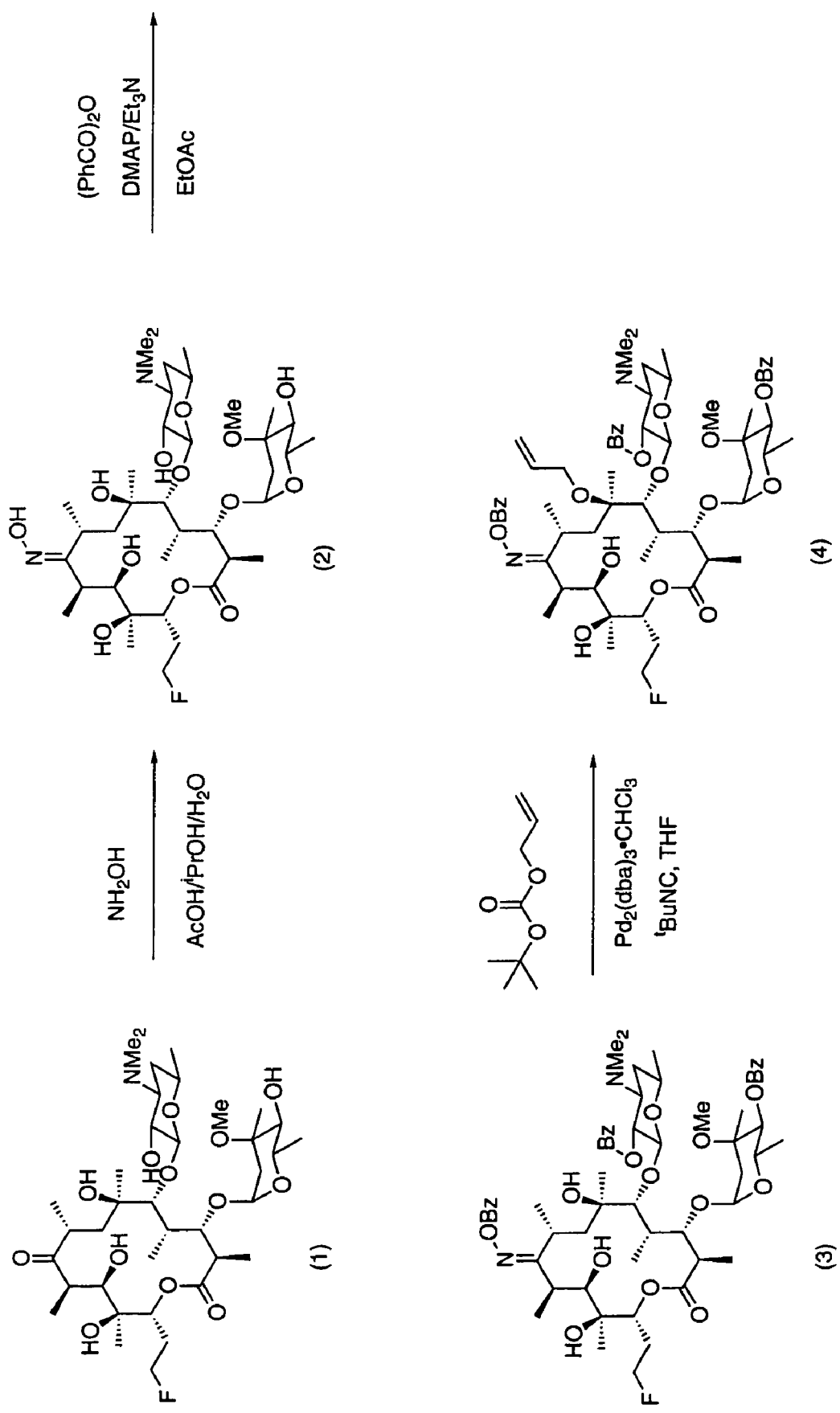
FIGS. 1A through 1D show methods for conversion of 15-fluoroerythromycin A into compounds of formula (I).

The present invention relates to antiinfective agents having improved safety and efficacy. These compounds are 7-quinolyl ketolide derivatives of 15-fluoroerythromycin. In one embodiment of the invention, compounds having the general structure (I) and pharmaceutically acceptable salts thereof are provided

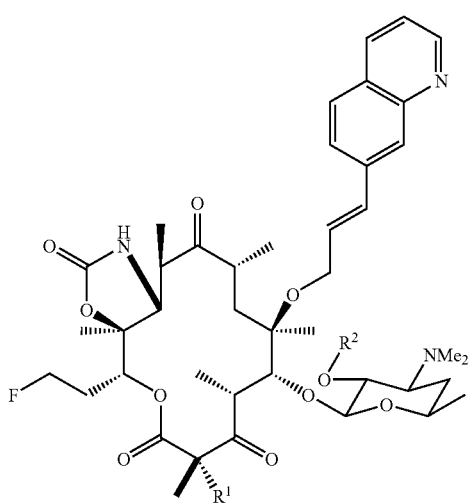

(I)

wherein $R^1$ is H or F and $R^2$ is H or a hydroxyl protecting group. By hydroxyl protecting group is meant a group commonly understood in the synthetic organic chemical art to be useful in masking the reactivity of a hydroxyl group. Such groups are detailed, for example, in Green and Wuts, *Protecting Groups in Organic Synthesis*, 3$^{rd}$ Ed., pp. 17-245, which is incorporated herein by reference. Selected examples of hydroxyl protecting groups include but are not limited to: acyl groups $R^3CO$, wherein $R^3$ is substituted or unsubstituted $C_1$-$C_5$ alkyl, substituted or unsubstituted aryl, or substituted or unsubstituted heteroaryl, for example formyl, acetyl, substituted acetyl, propionyl, benzoyl, methylsuccinyl, ethylsuccinyl, substituted benzoyl, nicotinoyl; and silyl ethers such as trimethylsilyl, triethylsilyl, tert-butyldimethylsilyl, triisopropylsilyl, dimethylthexylsilyl, tert-butyldiphenylsilyl, and the like. By substituted or unsubstituted $C_1$-$C_5$ alkyl is meant acyclic or cyclic, linear or branched hydrocarbyl groups of 1 to 5 carbon atoms, optionally substituted with one or more groups including halogen (F, Cl, Br, I), $C_1$-$C_5$ alkoxy, amino, $C_1$-$C_5$ alkylamino, di($C_1$-$C_5$ alkyl)amino, $C_1$-$C_5$ thioalkoxy, $C_6$-$C_{10}$ aryl, $C_1$-$C_{10}$ heteroaryl, ketone, carboxylate, ester, amide, and the like. By substituted or unsubstituted aryl is meant an aromatic hydrocarbyl group of 6 to 10 carbon atoms, for example phenyl or naphthyl, optionally substituted with one or more groups including halogen (F, Cl, Br, I), $C_1$-$C_5$ alkoxy, amino, $C_1$-$C_5$ alkylamino, di($C_1$-$C_5$ alkyl)amino, $C_1$-$C_5$ thioalkoxy, $C_6$-$C_{10}$ aryl, $C_1$-$C_{10}$ heteroaryl, ketone, carboxylate, ester, amide, and the like. By substituted or unsubstituted heteroaryl is meant a heteroaromatic group of 1 to 10 carbon atoms and comprising at least one N, O, or S atom, for example pyridyl, quinolyl, pyrrolyl, imidazolyl, furyl, thienyl, oxazolyl, thiazolyl, isoxazolyl, and the like, optionally substituted with one or more groups including halogen (F, Cl, Br, I), $C_1$-$C_5$ alkoxy, amino, $C_1$-$C_5$ alkylamino, di($C_1$-$C_5$ alkyl)amino, $C_1$-$C_5$ thioalkoxy, $C_6$-$C_{10}$ aryl, $C_1$-$C_{10}$ heteroaryl, ketone, carboxylate, ester, amide, and the like.

In one particular embodiment of the invention, compounds of formula (I) and pharmaceutically acceptable salts thereof wherein $R^1$ is H or F and $R^2$ is H or $R^3CO$, wherein $R^3$ is substituted or unsubstituted $C_1$-$C_5$ alkyl, substituted or unsubstituted aryl, or substituted or unsubstituted heteroaryl are provided.

In one embodiment of the invention, compounds of formula (I) are provided wherein $R^1$ is H. In one particular embodiment of the invention, compounds of formula (I) and pharmaceutically acceptable salts thereof wherein $R^1$ is H and $R^2$ is H or $R^3CO$, wherein $R^3$ is substituted or unsubstituted $C_1$-$C_5$ alkyl or substituted or unsubstituted aryl, are provided. In a more particular embodiment, compounds of formula (I) and pharmaceutically acceptable salts thereof wherein $R^1$ is H and $R^2$ is H or $R^3CO$, wherein $R^3$ is $CH_3$, $CH_3CH_2$, $CH_3CH_2O(C=O)CH_2CH_2$, or phenyl are provided.

In one embodiment of the invention, compounds of formula (I) are provided wherein $R^1$ is F. In one particular embodiment of the invention, compounds of formula (I) and pharmaceutically acceptable salts thereof wherein $R^1$ is F and $R^2$ is H or $R^3CO$, wherein $R^3$ is substituted or unsubstituted $C_1$-$C_5$ alkyl or substituted or unsubstituted aryl, are provided. In a more particular embodiment, compounds of formula (I) and pharmaceutically acceptable salts thereof wherein $R^1$ is F and $R^2$ is H or $R^3CO$, wherein $R^3$ is $CH_3$, $CH_3CH_2$, $CH_3CH_2O(C=O)CH_2CH_2$, or phenyl are provided.

In a more particular embodiment of the invention, compounds of formula (II) and (III) and pharmaceutically acceptable salts thereof are provided.

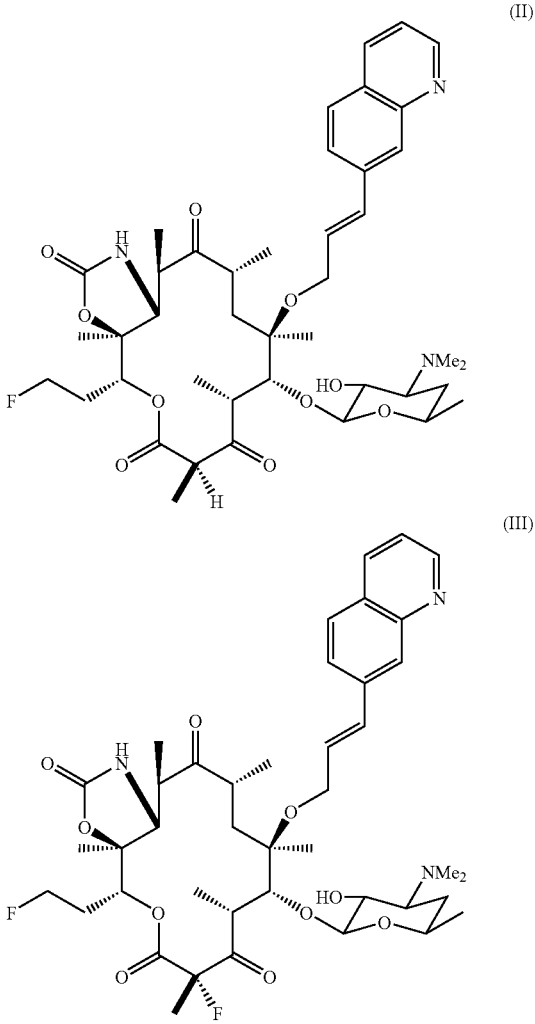

In another aspect of the invention, methods for the preparation of the compounds of formulae (I), (II), and (III) are provided. The compounds of formulae (I), (II), and (III) may be prepared starting from 15-fluoroerythromycin A, an analog of erythromycin A prepared using genetic engineering as disclosed, for example, in U.S. Pat. No. 6,492,562 (which is incorporated herein by reference) and as detailed below in Examples 1 through 5.

In one embodiment of the invention, 15-fluoroerythromycin A is converted into compounds of formulae (I), (II), and (III) as illustrated in FIGS. 1A to 1D, and particular illustrations of this embodiment are detailed below in Examples 6 through 20.

In one embodiment, illustrated in FIG. 1A, 15-fluoroerythromycin A (1) is first converted into the 9-oxime (2) by reaction with hydroxylamine in the presence of an acid catalyst, for example as described for erythromycin A in U.S. Pat. Nos. 5,274,085 and 5,808,017 (each of which is incorporated herein by reference). Suitable solvents include alcohols, such as methanol, ethanol, and isopropanol, or other water-miscible solvents. One illustration is detailed in Example 6 below.

Referring to FIG. 1A, the three most reactive hydroxyl groups in (2) are blocked, for example by acylation with an acid anhydride. Typical examples of acid anhydrides suitable include but are not limited to the anhydrides of substituted or unsubstituted $C_1$-$C_5$ carboxylic acids, for example acetic anhydride, propionic anhydride, formic-acetic anhydride, and similar, and anhydrides of aromatic carboxylic acids, for example benzoic anhydride and various substituted benzoic anhydrides. The anhydrides may be used directly or prepared in situ by reaction of a carboxylic acid with an activating agent such as a carboxylic acid halide. The acylation reaction with (2) is conducted in an inert solvent, for example ethyl acetate, tetrahydrofuran, dichloromethane, or similar solvents, in the presence of a base and an acylation catalyst. Suitable bases include amine bases, such as triethylamine, N-methylmorpholine, and similar, and suitable acylation catalysts include agents like 4-(dimethylamino)pyridine. Reaction temperatures may be from about 0° C. to about 50° C., preferably about 20° C. to about 30° C., and most preferably about 25° C. By "about" is meant within 5° C. of the indicated temperature ranges. One illustration using benzoic anhydride is detailed below in Example 7. Other protecting groups for the reactive hydroxyls may be used, for example silyl protecting groups such as trimethylsilyl, triethylsilyl, tert-butyl-dimethylsilyl, dimethylthexylsilyl, and the like, as described for erythromycin A oxime in U.S. Pat. No. 5,837,829 (incorporated herein by reference). In other embodiments, different protecting groups can be used for the oxime and the sugar hydroxyls, for example as described for the preparation of 6-O-methylerythromycin A in U.S. Pat. No. 5,852,180 (incorporated herein by reference). For example, the oxime hydroxyl may be protected as an ether, while the sugar hydroxyl groups can be protected by acylation or silylation as described above. Examples of suitable ether protecting groups for the oxime include but are not limited to benzyl ether and substituted benzyl ethers, and acetals such as 1-alkoxy-1-methylethyl ethers or 1-alkoxy-1-cyclohexyl ethers as described for erythromycin A oxime in U.S. Pat. No. 5,719,272 (incorporated herein by reference).

Referring to FIG. 1A, in one embodiment of the invention the resulting tribenzoate (3) is treated with an allylating reagent to produce the 6-O-allyl intermediate (4). Suitable allylating agents include allyl halides such as allyl bromide, allyl chloride, and allyl iodide, together with a strong base such as potassium tert-butoxide, sodium bis(trimethylsilyl) amide (NaHMDS), or potassium bis(trimethylsilyl)amide (KHMDS), as described for erythromycin A derivatives in U.S. Pat. Nos. 5,866,549 and 6,395,710 (each of which is incorporated herein by reference), or an allyl carbonate or carbamate such as allyl tert-butyl carbonate in the presence of a metal catalyst, such as a palladium/phosphine catalyst as described for erythromycin A in U.S. Pat. No. 6,437,106 (incorporated herein by reference), or a molybdenum or tungsten catalyst together with a suitable ligand. In certain embodiments, the allylating reagent is allyl tert-butyl carbonate in the presence of a metal catalyst formed from a palladium species, including but not limited to palladium acetate, palladium bromide, allylpalladium chloride, and dipalladium tris(benzylidenacetone) ($Pd_2(dba)_3$) or its chloroform adduct, together with a phosphine, arsine, or isocyanide ligand. In one particular illustration, shown in FIG. 1A and detailed in Example 8 below, the allylating reagent is allyl tert-butyl carbonate in the presence of a metal catalyst formed from dipalladium tris(benzylidenacetone) ($Pd_2(dba)_3$) or its chloroform adduct and an isocyanide ligand, for example tert-butyl isocyanide.

Thus in one aspect of the invention, a method for preparing a compound of formula (IV), an intermediate for the preparation of compounds of formula (I), is provided (IV)

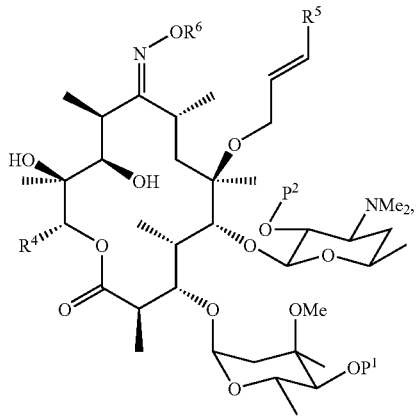

wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $R^5$ is H, unsubstituted or substituted heteroaryl, or unsubstituted or substituted aryl; $P^1$ and $P^2$ are each independently hydroxyl protecting groups; and $R^6$ is a hydroxyl protecting group; is provided, the method comprising the step of reacting a compound of formula (V)

(V)

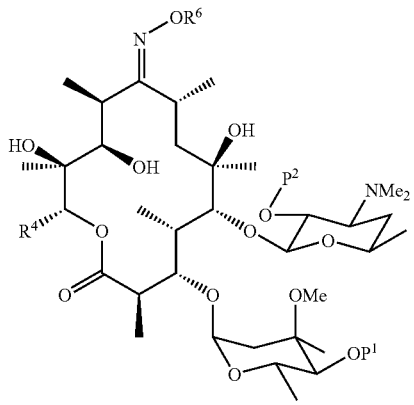

wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $P^1$ and $P^2$ are each independently hydroxyl protecting groups; and $R^6$ is a hydroxyl protecting group; with a compound of formula (VIa), (VIb), or (VIc)

(VIa)

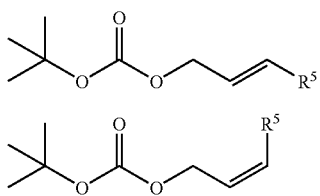

(VIb)

-continued (VIc)

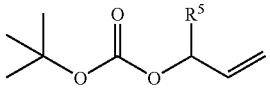

wherein $R^5$ is H, unsubstituted or substituted heteroaryl, or unsubstituted or substituted aryl; in the presence of a metal catalyst having an isocyanide ligand.

The preparation of compounds of formula (V) is known in the art, for example as described in U.S. Pat. Nos. 6,395,710; 6,451,768; 6,794,366; 6,399,582; 6,458,771; 6,590,083; 6,395,710; 6,593,302; 6,514,944; and 6,762,168 (each of which is incorporated herein by reference), or as described in the working examples below. The preparation of compounds of formula (VIa), (VIb), and (VIc) is also known in the art, for example as described in U.S. Pat. Nos. 6,417,366 and 6,579,986 (each of which is incorporated herein by reference). Suitable metal catalysts include but are not limited to palladium acetate, palladium bromide, allylpalladium chloride, and dipalladium tris(benzyliden-acetone) (Pd$_2$(dba)$_3$) or its chloroform adduct.

In a particular embodiment of the invention, a method of preparing compounds of formula (IV), wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $R^5$ is H, unsubstituted or substituted heteroaryl, or unsubstituted or substituted aryl; $P^1$ and $P^2$ are each independently hydroxyl protecting groups; and $R^6$ is a hydroxyl protecting group is provided wherein the metal catalyst comprises palladium having an isocyanide ligand.

In a more particular embodiment of the invention, a method of preparing compounds of formula (IV), wherein $R^4$ is unsubstituted or substituted $C_1$-$C_8$ alkyl, unsubstituted or substituted $C_2$-$C_8$ alkenyl, $C_2$-$C_8$ alkynyl, unsubstituted or substituted heteroaryl, or unsubstituted or substituted aryl; $R^5$ is H, unsubstituted or substituted heteroaryl, or unsubstituted or substituted aryl; $P^1$ and $P^2$ are each independently hydroxyl protecting groups; and $R^6$ is a hydroxyl protecting group is provided, wherein the metal catalyst comprises palladium having a tert-butylisocyanide ligand.

In a more particular embodiment of the invention, a method of preparing compounds of formula (IV), wherein $R^4$ is unsubstituted or substituted $C_1$-$C_8$ alkyl; $R^5$ is H, unsubstituted or substituted heteroaryl, or unsubstituted or substituted aryl; $P^1$ and $P^2$ are each independently hydroxyl protecting groups; and $R^6$ is a hydroxyl protecting group is provided, wherein the metal catalyst comprises palladium having a tert-butylisocyanide ligand.

In a more particular embodiment of the invention, a method of preparing compounds of formula (IV), wherein $R^4$ is unsubstituted or substituted $C_1$-$C_8$ alkyl; $R^5$ is H; $P^1$ and $P^2$ are each independently hydroxyl protecting groups; $R^6$ is a hydroxyl protecting group is provided, wherein the metal catalyst comprises palladium in the presence of tert-butylisocyanide.

In a more particular embodiment of the invention, a method of preparing compounds of formula (IV), wherein $R^4$ is $CH_2CH_2F$; $R^5$ is H; and $P^1$, $P^2$, and $R^6$ are each benzoyl, and the metal catalyst comprises palladium having a tert-butylisocyanide ligand is provided.

Figure 1B:
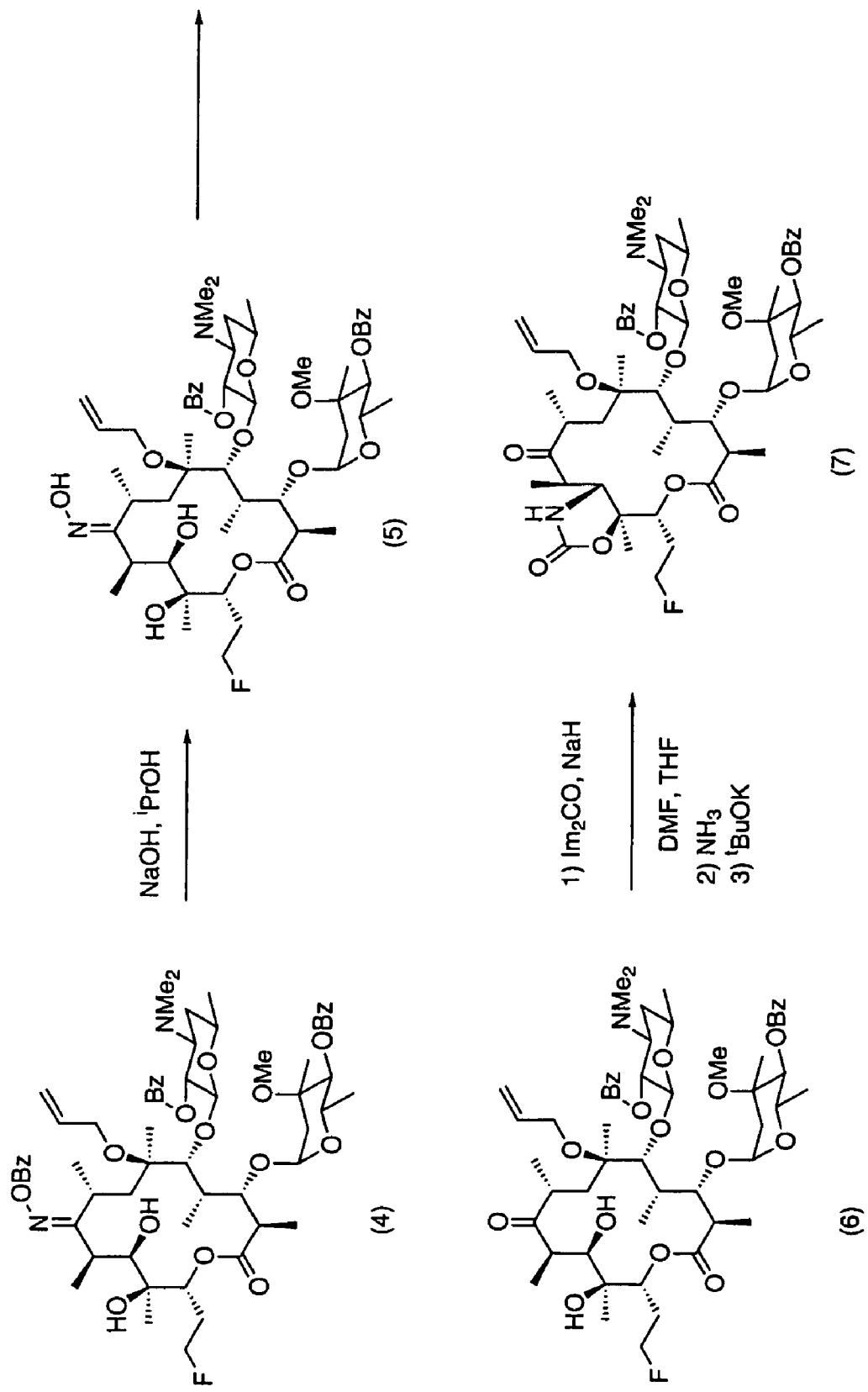

Referring to FIG. 1B, in other embodiments of the invention, the protected oxime in 6-O-allyl intermediate (4) is deprotected, for example by treatment with alkali in an alcoholic solvent as detailed below in Example 9, to produce oxime (5). Removal of the oxime to produce ketone (6) may be accomplished by any number of means known in the art, for example by (i) reductive hydrolysis using $Na_2S_2O_4$ and $HCO_2H$ in a mixture of an alcohol or tetrahydrofuran and water as illustrated below in Example 10 and in U.S. Pat. No. 6,395,710 (incorporated herein by reference); (ii) by hydrolysis using $NaHSO_3$ and an acid, for example a carboxylic acid such as acetic acid or levulinic acid, in a mixture of an alcohol or tetrahydrofuran and water; (iii) by reduction of the oxime to an imine, for example using $TiCl_3$ buffered by addition of ammonium acetate, followed by hydrolysis of the imine by treatment with aqueous acid; (iv) oxidative hydrolysis, for example by treatment with $NaNO_2$ in aqueous acid; or (v) by treatment with a disulfide such as phenyldisulfide and a phosphine such as tributylphosphine to produce the thioimine, which is subsequently hydrolyzed to the imine and then the ketone by treatment with aqueous acid as described for erythromycin A oximes in U.S. Pat. No. 6,455,608 (incorporated herein by reference).

Again referring to FIG. 1B, the ketone (6) is converted into the 11,12-cyclic carbamate (7). In one particular embodiment of the invention, ketone (6) is treated with a molar excess of a carbonylating reagent, for example 1,1-carbonyldiimidazole, in the presence of a strong base, such as sodium hydride or NaHMDS, as described for erythromycin A derivatives in U.S. Pat. No. 6,437,106 (incorporated herein by reference). In a preferred embodiment, the base is sodium hydride as illustrated in Example 11 below. Use of sodium hydride rather than NaHMDS avoids formation of a 10,11-anhydro-12-O-(trimethylsilyl) side product. The resulting intermediate is treated with ammonia followed by potassium tert-butoxide to provide cyclic carbamate (7).

Figure 1C:
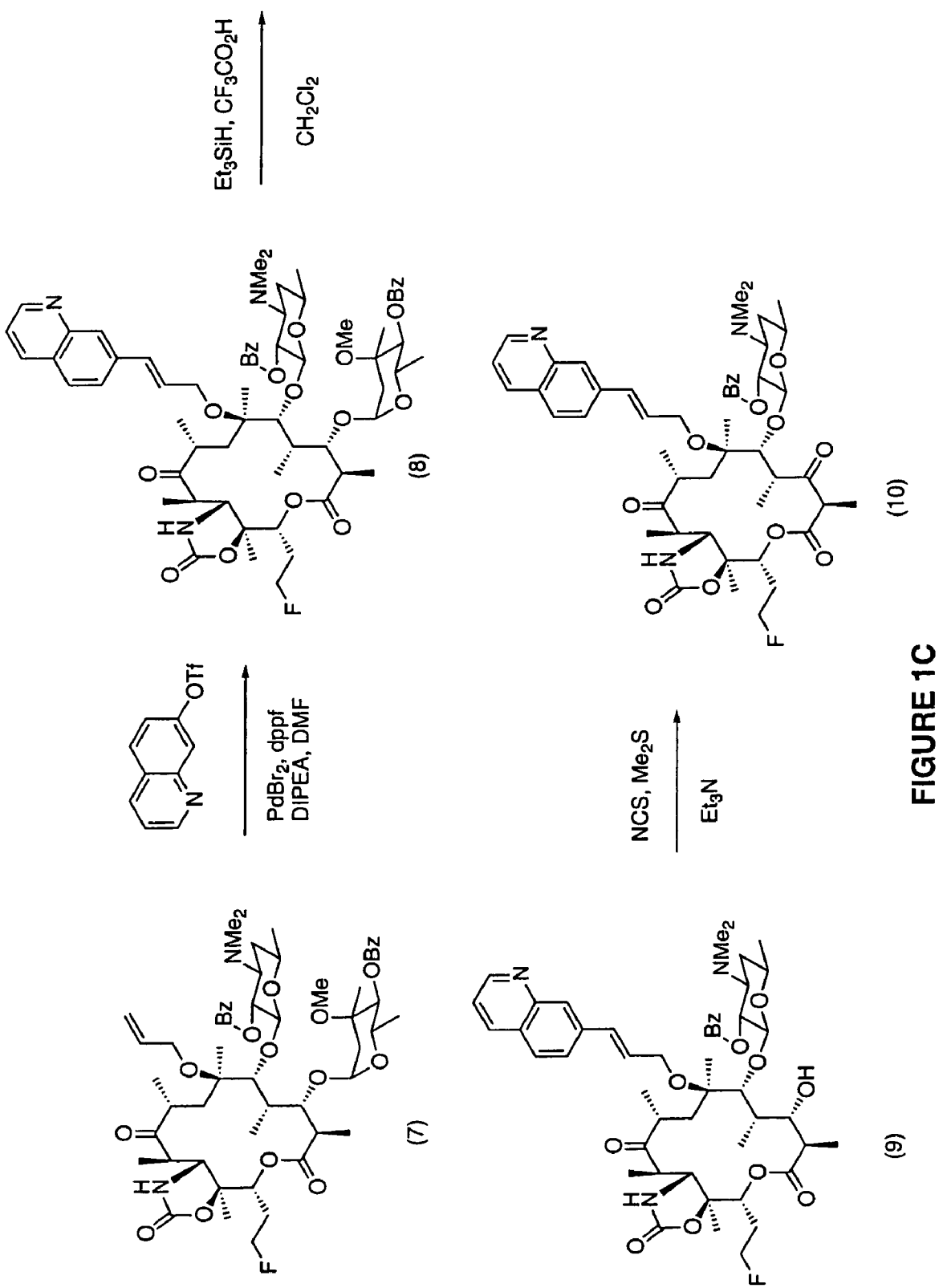

Referring to FIG. 1C, in one embodiment of the invention, cyclic carbamate (7) is treated with an arylating reagent under Heck coupling conditions to produce the 7-quinolyl intermediate (8). Suitable arylating reagents include compounds of formula (VII)

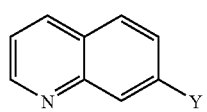

(VII)

wherein Y is Cl, Br, I, $OSO_2R^7$, and $OPO(OR^7)_2$, wherein $R^7$ is substituted or unsubstituted $C_1$-$C_4$ alkyl or substituted or unsubstituted aryl. In particular embodiments, Y is Br or $OSO_2R^7$, wherein $R^7$ is substituted or unsubstituted $C_1$-$C_4$ alkyl or substituted or unsubstituted aryl. In more particular embodiments, Y is Br or $OSO_2CF_3$. In an even more particular embodiment, Y is $OSO_2CF_3$. The arylating reagent is reacted with cyclic carbamate (7) in the presence of a suitable catalyst and a base under conditions where the Heck coupling occurs. In one particular embodiment of the invention, the catalyst is a palladium catalyst, for example $PdBr_2$, $Pd_2(dba)_3$, $Pd_2(dba)_3 \cdot CHCl_3$, $Pd(OAc)_2$, $Pd(Ph_3P)_4$, or similar, together with a suitable ligand, for example 1,4-bis(diphenylphosphino)-butane (dppb), 1,1'-bis(diphenylphosphino) ferrocene (dppf), triphenylphosphine, or triphenylarsine. The catalyst may also be a metal bound to a solid support or encapsulated. Suitable bases include trialkylamine bases, such as triethylamine, N-methylmorpholine, and N,N-diisopropylethylamine, as well as inorganic bases such as $LiHCO_3$, $Li_2CO_3$, $NaHCO_3$, $Na_2CO_3$, $KHCO_3$, $K_2CO_3$, NaOAc, KOAc, $Cs_2CO_3$, and the like. In another embodiment of the invention, the Heck coupling can be performed in the absence of phosphine ligand under conditions similar to those described in U.S. Patent Publication 2003/0125531, which is incorporated herein by reference. In a particular embodiment of the invention, illustrated in Example 12 below, cyclic carbamate (7) is reacted with 7-quinolyl triflate in the presence of $PdBr_2$ and dppf in dimethylformamide at a temperature of about 80° C. to produce quinolyl intermediate (8).

Compounds of formula (IV) may be prepared according to procedures known in the art. In one embodiment of the invention, the compound of formula (IV) wherein Z is $OSO_2CF_3$ is prepared as illustrated in Example 18 below by reaction of commercially available 7-hydroxyquinoline with triflic anhydride in pyridine.

Again referring to FIG. 1C, the quinolyl intermediate (8) is converted into descladinosyl intermediate (9). In one embodiment of the invention, descladinosyl intermediate (9) is formed under non-aqueous conditions by reaction of intermediate (8) with an acid in the presence of a hydride source. In a particular embodiment, the acid is trifluoroacetic acid and the hydride source is a silane such as triethylsilane or tert-butyldimethylsilane, as illustrated in Example 13 below. The solvent may be any compatible anhydrous solvent, such as dichloromethane, chloroform, dichloroethane, toluene, benzene, and similar. In other embodiments of the invention, the cladinosyl group is removed using aqueous acid, for example as described for erythromycin A derivatives in U.S. Pat. Nos. 6,395,710 and 6,437,106 (each of which is incorporated herein by reference).

Again referring to FIG. 1C, descladinosyl intermediate (9) is converted into ketone (10), a compound of formula (I) wherein $R^1$ is H and $R^2$ is a hydroxyl protecting group, by oxidation of the 3-hydroxyl group. In one embodiment illustrated in Example 14 below, the oxidation uses the Corey-Kim reagent (N-chlorosuccinimide and methylsulfide) in an inert solvent such as dichloromethane. In other embodiments, the oxidation uses Pfizer-Moffat conditions (a carbodiimide and methylsulfoxide with a mild acid catalyst), Swern conditions (oxalyl chloride, methylsulfoxide, and triethylamine), or similar methods known in the art for erythromycin A derivatives.

Figure 1D:
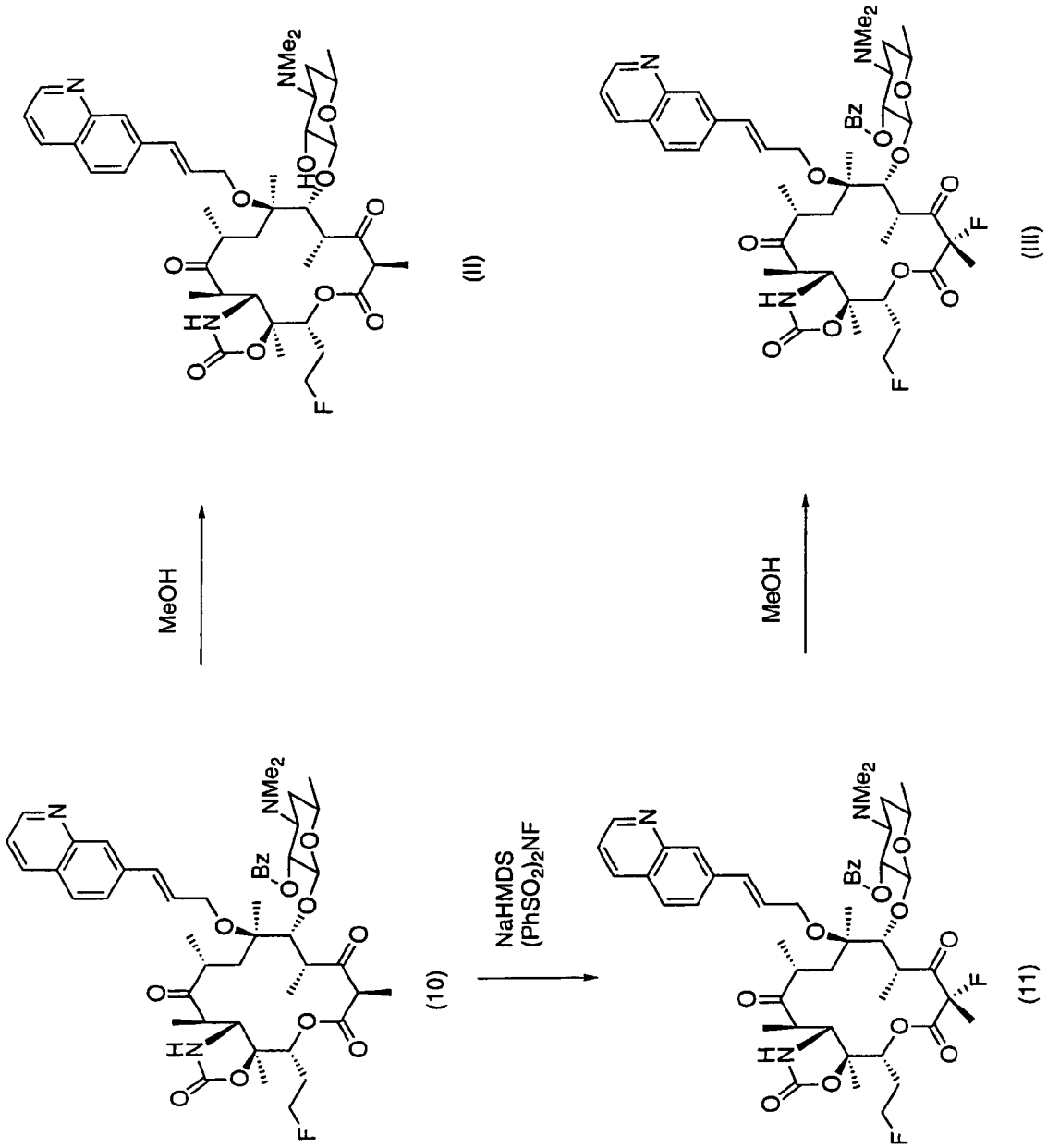

Referring to FIG. 1D, ketone (10) can optionally be converted into the 2-fluoro derivative (11) by treatment with a strong base and a fluorinating agent, using methods similar to those described for erythromycin A derivatives in U.S. Pat. No. 6,124,269 (incorporated herein by reference). In one embodiment, the base is NaHMDS and the fluorinating agent is N-fluorobenzenesulfonimide, as illustrated in Example 16 below.

Compounds of formula (I) wherein $R^1$ is H or F and $R^2$ is a hydroxyl protecting group typically do not have potent antibacterial activity, yet may be useful as prodrug forms of the compounds of formula (I) wherein $R^1$ is H or F and $R^2$ is H. In one embodiment of the invention, compounds of formula (I) wherein $R^1$ is H or F and $R^2$ is $R^3CO$, wherein $R^3$ is substituted or unsubstituted $C_1$-$C_5$ alkyl or substituted or unsubstituted aryl, are provided as prodrug forms. Upon administration to a patient, chemical or enzymatic deprotection occurs in vivo so as to form compounds of formula (I) wherein $R^1$ is H or F and $R^2$ is H. Such prodrugs often show improved absorption, stability, and/or pharmacokinetic behavior. In a particular embodiment of the invention, compounds of formula (I) wherein $R^1$ is H or F and $R^2$ is $CH_3CO$, $CH_3CH_2CO$, and $CH_3CH_2O(C=O)CH_2CH_2CO$ are provided.

Compounds of formula (I) wherein $R^1$ is H or F and $R^2$ is a hydroxyl protecting group may optionally be converted into compound of formula (I) wherein $R^1$ is H or F and $R^2$ is H by deprotection using methods known in the art. In one embodiment, illustrated in FIG. 1D, $R^2$ is $R^3CO$, and the deprotection is conveniently performed by treatment of the protected form with methanol at temperatures between 20° C. and 65° C., as described for related compounds in U.S. Pat. No. 6,395,710 (incorporated herein by reference) and illustrated below in Examples 15 and 17.

In another embodiment of the invention, compounds of formula (I) wherein $R^2$ is H are converted into compounds of formula (I) wherein $R^2$ is a hydroxyl protecting group by methods known in the art. For example, compounds of formula (I) wherein $R^2$ is H are treated with acid anhydrides $(R^3CO)_2O$ to form compounds of formula (I) wherein $R^2$ is $R^3CO$, illustrated in Examples 19 and 20 below. Such compounds may be useful as prodrug forms of the antibacterial compounds.

In another embodiment of the invention, pharmaceutically acceptable salts of the compounds of formula (I) are provided. Pharmaceutically acceptable salts of these compounds include but are not limited to: halide salts such as hydrochlorides, hydrobromides, and hydroiodides; sulfate and sulfonate salts such as bisulfates, sulfates, mesylates, tosylates, taurates, and lauryl sulfates; carboxylates such as maleates, fumarates, acetates, propionates, stearates, and lactobionates; nitrates, phosphates, and similar.

As shown below in Examples 21 and 23 and in Tables 11 and 13, compounds (II) and (III) have excellent in vitro activity against a range of bacteria. In particular, these compounds show potent antibacterial activity against bacteria involved in both pulmonary disease such as pneumonia (such as *Streptococcus pneumoniae* and *Haemophilus influenzae*) and skin infections such as acne (such as *Propionibacterium acnes* and *P. granulosum*), including organisms that are highly resistant to traditional macrolides such as erythromycin A and agents such as clindamycin. As demonstrated in Example 22 and Table 12, compounds (II) and (III) show excellent in vivo activity, inhibiting the growth of *Streptococcus pneumoniae* in infected rat lungs after oral dosing and increasing survival.

Examples 24-27 demonstrate the unexpected superiority of compounds (II) and (III) in comparison with comparator compounds of formula (VIII):

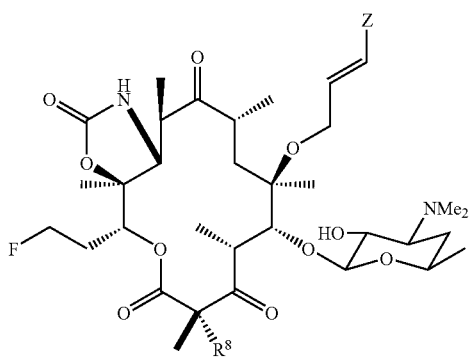

wherein $R^8$ is H or F and Z is 3-quinolyl, 6-quinolyl, 6-quinoxalyl, or 1,5-naphthyrid-3-yl.

Example 27 details the pharmacokinetic profiles of compounds of formula (VIII) wherein $R^8$ is H or F and Z is 3-quinolyl, 6-quinoxalyl, and compounds of the invention having formulas (II) and (III) in the mouse model. As shown in Table 18, compound (III) shows unexpectedly high maximal plasma concentrations ($C_{max}$) and total exposures (determined by the area under the curve, AUC) compared with comparator compounds in both mouse plasma and mouse lung tissue.

Attainment of high plasma and lung tissue levels and total exposures of drug are particularly important for the treatment of pulmonary infections, such as pneumonia, where pathogens infect not only the epithelial lining fluid but also the tissues. For macrolide therapy, the efficacy of treatment is related to the $C_{max}$/MIC and AUC/MIC ratios, such that increases in these ratios in both the plasma and tissues correlates with therapeutic success.

Figure 2:
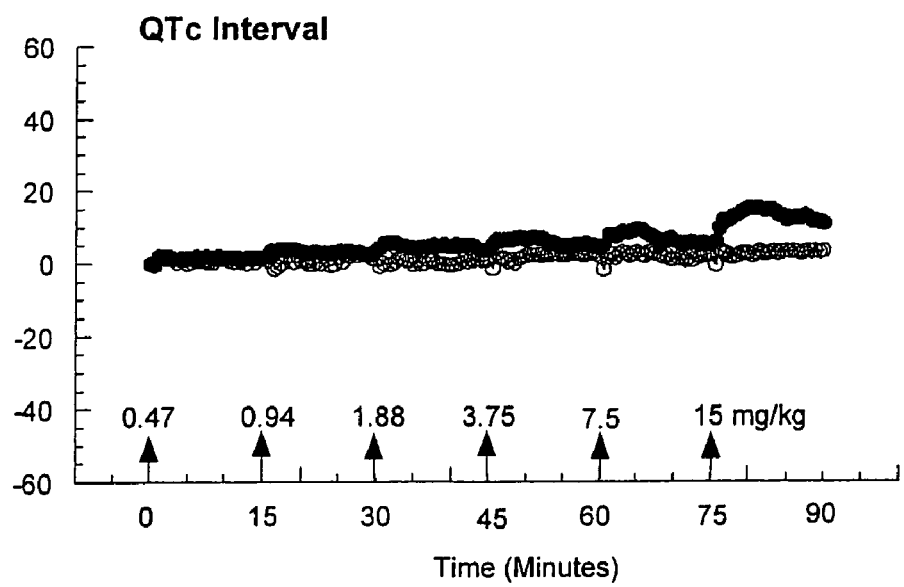
FIGS. 2A and 2B show the effects of intravenous doses of comparator 15-fluoroketolides on the QTc interval of the electrocardiogram of anesthetized guinea pigs. The indicated injections were made and the resulting % change from baseline of the QT interval corrected for heart rate is shown. Filled circles show results from ketolide injection, while open circles show results from vehicle injection.
Figure 2:
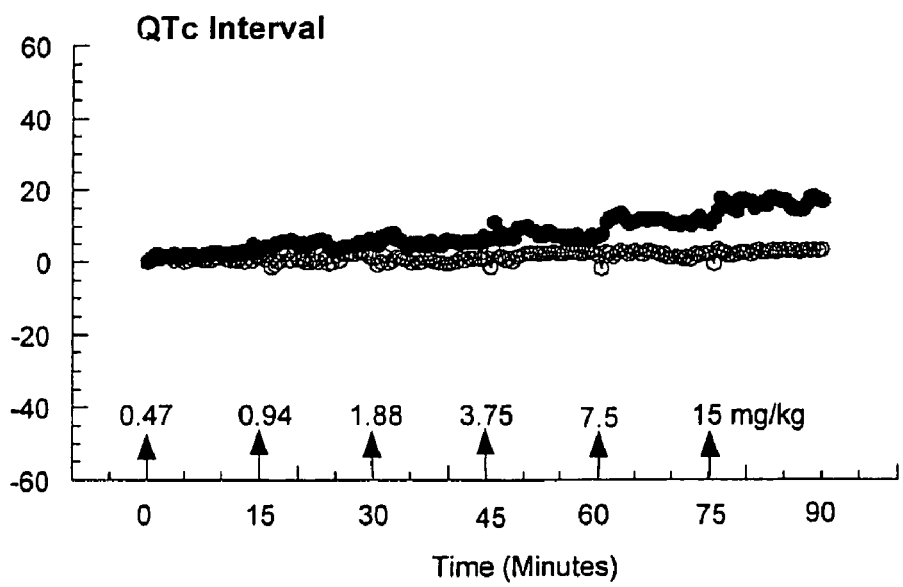
Figure 3:
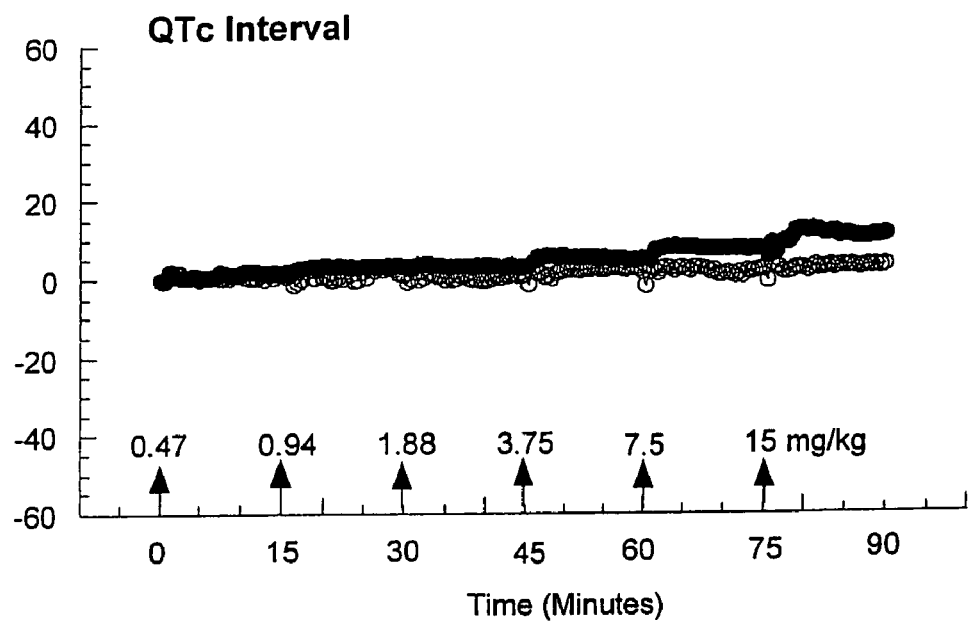
FIGS. 3A and 3B show the effects of intravenous doses of comparator 15-fluoroketolides on the QTc interval of the electrocardiogram of anesthetized guinea pigs. The indicated injections were made and the resulting % change from baseline of the QT interval corrected for heart rate is shown. Filled circles show results from ketolide injection, while open circles show results from vehicle injection.
Figure 3:
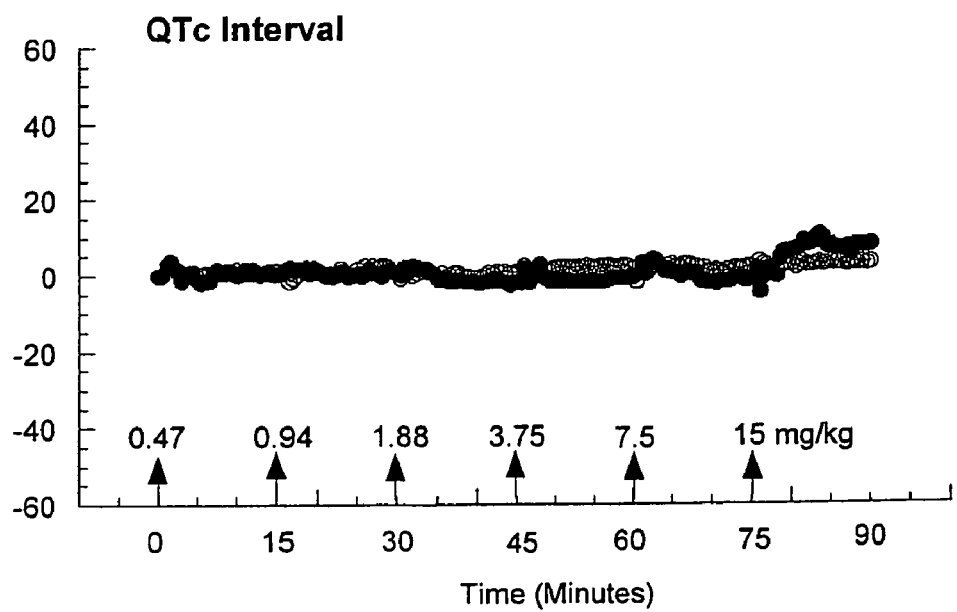
Figure 4:
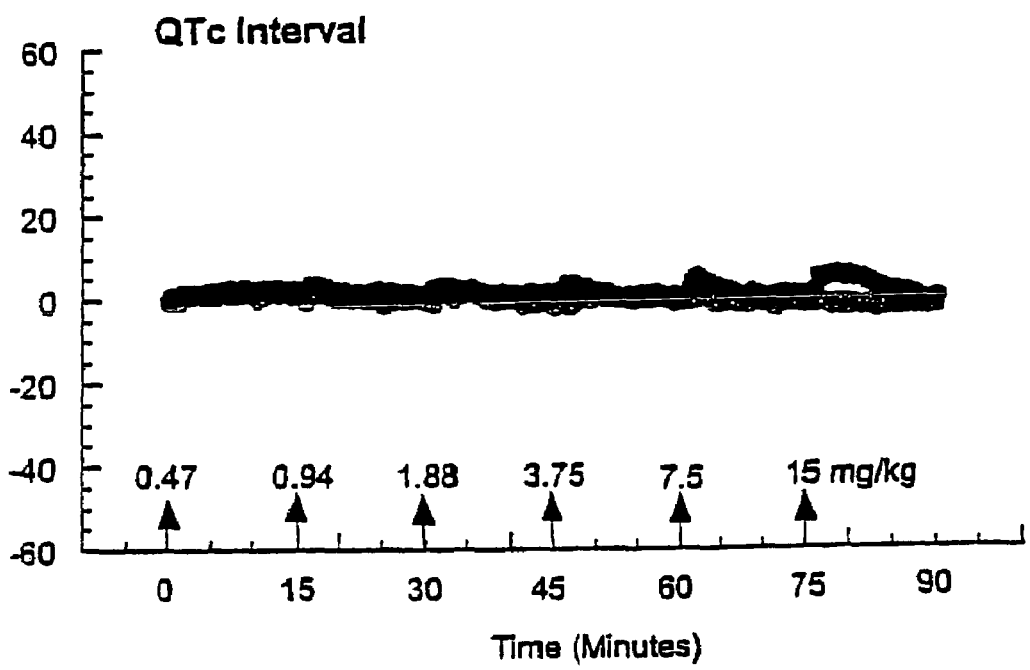
FIGS. 4A and 4B show the effects of intravenous doses of 15-fluoroketolides on the QTc interval of the electrocardiogram of anesthetized guinea pigs. The indicated injections were made and the resulting % change from baseline of the QT interval corrected for heart rate is shown. Filled circles show results from ketolide injection, while open circles show results from vehicle injection.
Figure 4:
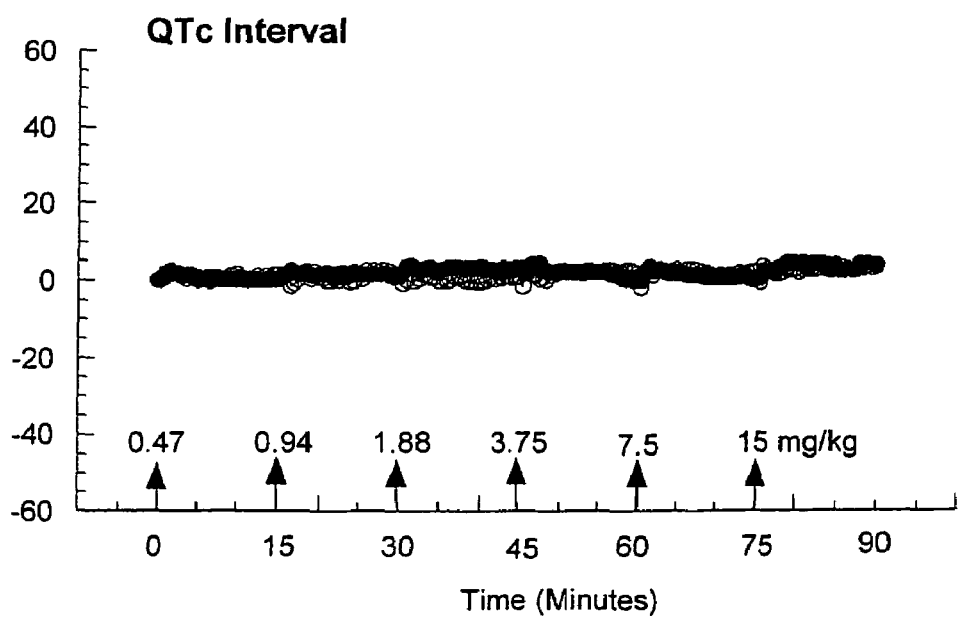

As noted above, one characteristic of macrolides is their ability to prolong the QT interval in the electrocardiogram (ECG). QT prolongation is associated with induction of torsade de pointes and cardiac arrest in a susceptible segment of the population. Typically, such effects are determined by dosing of appropriate test animals with increasing levels of drug and monitoring the EKG and related parameters such as heart rate and arterial pressure. As detailed in Examples 24 and 25 below, 15-fluoroketolides having a variety of heterocyclic groups were studied in several animal models. In the rat, the compound of the invention having formula (II) and (III) did not prolong the QT interval, whereas the comparator ketolides showed increases in the QT interval (Table 14). In the anesthetized guinea pig (Table 15), comparator compounds of formula (VIII) wherein Z is 3-quinolyl, 6-quinolyl, or 1,5-naphthyrid-3-yl and $R^8$=H showed pronounced, dose-dependent prolongation of the QT interval (measured as the QT interval corrected for changes in heart rate, QTc) that persisted post-injection as shown in FIGS. 2 and 3. The compound wherein Z is 3-quinolyl and $R^8$ is F showed a smaller yet persistent increase in QTc at the highest dose (FIG. 3). The compound wherein Z is 6-quinoxalyl showed a moderate, dose-dependent increase in the QTc interval that slowly returned to baseline (FIG. 4). In contrast, the compound of the invention having formula (II) showed no statistically significant effects on the QTc interval or related parameters at cumulative doses up to 30 mg/kg in the guinea pig relative to vehicle controls.

Comparator compounds of formula (VIII) wherein Z is 3-quinolyl or 6-quinoxalyl, together with compounds of the invention having formulas (II) and (III) were further investigated in models of hepatotoxicity. In these assays, compounds were applied to hepatocytes in cell culture, and the minimum concentration needed to induce effects on metabolic stability and steatosis (lipid accumulation) was determined. As detailed in Example 26 below, the compound of formula (VIII) wherein Z is 3-quinolyl affected metabolic stability and steatosis in human HepG2 hepatocytes at 30 μM. No effects were observed with the compounds wherein Z is 6-quinoxalyl or with compounds of the invention having formulas (II) and (III) at 100 μM. Further testing of compound (III) against primary human hepatocytes revealed no cytotoxicity at concentrations up to 200 μM.

Based on the above results compounds of formula (VIII) wherein Z is 6-quinoxalyl were further compared to compounds of the invention in dog models to evaluate safety. Surprisingly, the compound wherein Z is 6-quinoxalyl and $R^8$ is F proved extremely toxic, with severe clinical effects being observable upon intravenous dosing at only 9 mg/kg. In contrast, both compounds (II) and (III) could be dosed intravenously up to at least 30 mg/kg. Further study of compounds (II) and (III) using telemetered dogs (Example 25) revealed no effects on cardiac parameters, including QT interval, upon intravenous infusion up to 15 mg/kg, at which point the measured plasma concentrations of drug exceeded the anticipated therapeutic level by approximately 5-fold. Further study with compound (III) showed no significant effect relative to vehicle at 30 mg/kg.

Thus, we have unexpectedly found that 15-fluoroketolides having a 7-quinolyl heterocyclic group have beneficial properties making them useful in the treatment of bacterial infections. In particular, compounds of the invention having formulas (II) and (III) show an unanticipated combination of activity and safety relative to related compounds. In particular, compound (III) shows unexpectedly good pharmacokinetics combined with high activity and a good cardiac and hepatic safety profile.

This invention further provides methods of treating bacterial infections, or enhancing the activity of other anti-bacterial agents, in warm-blooded animals, in particular in mammals, and especially in humans, which comprise administering to the animals or humans one or more compounds of formula (I) alone or in admixture with a diluent or in the form of a medicament according to the invention. For use in treating infectious disease, the compounds of the invention are formulated into suitable compositions which will include typical excipients, pharmaceutically acceptable counterions if the compound is a salt, further additives as desired, such as antioxidants, buffers, and the like, and administered to animals or humans. The compounds can be administered by any desired route, including injection, oral administration, transdermal administration, transmucosal administration, or any combination. The compounds of the invention can also be administered with additional active ingredients if desired.

Compounds of this invention are suitable for the treatment of bacterial infections of the skin and respiratory tract. Compounds of this invention are especially suitable for treatment of infections caused by *Streptococcus pneumoniae, Streptococcus pyogenes, Moraxella catarrhalis, Haemophilus influenzae, Propionibacterium acnes*, and *Propionibacterium granulosum*. As demonstrated in Examples 21 and 23 below, compounds (II) and (III) retain potent activity against pathogens that are resistant to either erythromycin, clarithromycin, or clindamycin.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical compositions may contain, for example, from about 0.5% up to about 90% of the active ingredient in combination with the carrier, more usually between 0.5% and 60% by weight.

Compositions for topical application may take the form of liquids, creams, foams, ointments, or gels, comprising a therapeutically effective concentration of a compound of the invention admixed with a dermatologically acceptable carrier. In one embodiment of the invention, the therapeutically effective concentration ranges from about 0.05% to about 5% (w/v). In a further embodiment of the invention, the therapeutically effective concentration ranges from about 0.1% to about 3% (w/v). In an even further embodiment of the invention, the therapeutically effective concentration is selected from the group consisting of 0.5%, 1% and 2% (w/v). As described in the Examples below, various dermatologically acceptable carriers may be used for topical formulations comprising the compounds of the invention, including but not limited to ethanol, propylene glycol, benzyl alcohol, transcutol, and dibutyl sebacate. Particularly effective compositions for compound (III) have been found that comprise dibutyl sebacate, as illustrated below in Example 28.

In other embodiments of the invention, compositions for topical application further comprise other anti-bacterial and/or anti-inflammatory agents. In particular embodiments of the invention, compositions for topical application further comprise benzoyl peroxide or a retinoid, for example retinoic acid, tretinoin, adapalene, tazarotene, or similar compounds.

In preparing the compositions in oral dosage form, any of the usual pharmaceutical media may be employed. Solid carriers include starch, lactose, dicalcium phosphate, microcrystalline cellulose, sucrose, and kaolin, while liquid carriers include sterile water, polyethylene glycols, non-ionic surfactants and edible oils such as corn, peanut and sesame oils, as are appropriate to the nature of the active ingredient and the particular form of administration. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The active compounds may also be administered parenterally or intraperitoneally. Solutions or suspensions of these active compounds as a free base or pharmacologically acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol, or liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 100 mg/kg of animal or human body weight, preferably given once a day, or in divided doses two to four times a day, or in sustained release form. For most large mammals, including humans, the total daily dosage is from about 0.05 g to 5.0 g, preferably from about 100 mg to 1000 mg. Dosage forms suitable for internal use comprise from about 100 mg to 500 mg of the active compound in intimate admixture with a solid or liquid pharmaceutically acceptable carrier. This dosage regiment may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredient(s) with the diluent(s) to form a pharmaceutical composition (e.g., a granulate) and then forming the composition into the medicament (e.g., tablets).

The compounds of the invention and their salt forms, and pharmaceutical compositions comprising the compounds of the invention, are useful in the control of infections. Given their microbiological activities and pharmacokinetic properties, they are particularly useful in the control of pulmonary infections, for example pneumonia, bronchitis, bronchiolitis, tonsillitis, and pharyngitis resulting from infection with *Streptococcus pneumoniae, Streptococcus pyogenes,* and *Haemophilus influenzae*, for example. The compounds of the invention and their salt forms, and pharmaceutical compositions comprising the compounds of the invention, are further useful in the control of skin infections, such as those resulting from infection by *Staphylococcus aureus* and various species of *Streptococcus*, and acne resulting from *Propionibacterium acnes* and *Propionibacterium granulosum*. The compounds of the invention and their salt forms, and pharmaceutical compositions comprising the compounds of the invention, are further useful in the control of ocular infections, for example keratitis and conjunctivitis. In particular, the compounds of the invention are useful in the treatment of infections caused by microorganisms that are resistant to erythromycin, clarithromycin, azithromycin, and related macrolide antibacterial agents.

A detailed description of the invention having been provided above, the following examples are given for the purpose of illustrating the present invention and shall not be construed as being a limitation on the scope of the invention or claims.

EXAMPLE 1

3-Fluoropropanal

Trichloroisocyanuric acid (17.0 g, 73 mmol) was added in ~1 g portions over 1 hour to a vigorously stirred mixture of 3-fluoropropanol (15.6 g, 200 mmol), NaHCO$_3$ (16.8 g, 200 mmol), and TEMPO (0.35 g, 2.2 mmol) in CH$_2$Cl$_2$ (300 mL) and water (10 mL). The temperature was kept at 20~25° C. using a water bath. After addition was complete, the mixture was stirred until the orange color fades to a pale yellow (approximately 30 minutes). The resulting solution was decanted from the gummy white residue, filtered through a pad of silica gel (5 g), and dried over MgSO$_4$ (10 g) for 30 minutes to provide a solution of 3-fluoropropanal in CH$_2$Cl$_2$. The concentration was determined by $^1$H-NMR as described for 3-chloropropanal above using the formula:

[3-fluoropropanal]=(integral of δ 9.83)/(integral of δ 5.28)*31.2

This procedure provided an approximately 0.5 M solution of 3-fluoropropanal in CH$_2$Cl$_2$, which was stable for several weeks when stored at –20° C.

EXAMPLE 2

N-[(2R*,3S*)-5-fluoro-3-hydroxy-2-methylpentanoyl]-2-benzoxazolone

Titanium tetrachloride (15.8 mL, 144 mmol) was added over 5 minutes to a vigorously stirred solution of N-propionyl-2-benzoxazolone (25.0 g, 131 mmol) in anhydrous CH$_2$Cl$_2$ (250 mL) cooled on ice and maintained under inert atmosphere. After 10 minutes, the yellow slurry was treated with N-methylmorpholine (15.8 mL, 144 mmol) over 5 minutes, and stirring was continued for an additional 45 minutes. A 0.48 M solution of 3-fluoropropanal (310 mL, 150 mmol) was added to the dark red solution over 30 minutes, such that the internal temperature remained below 10° C. After addition was complete, the mixture was stirred for an additional 30 minutes on ice, then at warm to ambient temperature an additional 1 hour. The reaction was treated with 250 mL of 2 N HCl with vigorous mixing, and the phases were separated, discarding the aqueous phase. The organic phase was filtered through a pad of silica gel (10 g), which was subsequently washed with 100 mL of methyl tert-butyl ether (MTBE). The combined eluates were evaporated to dryness. The resulting solid mass was triturated with MTBE, allowed to stand for 1 hour, then collected by vacuum filtration, yielding 26 gm of crystalline product. $^1$H-NMR: δ 8.07-8.02 (m, 1H), 7.29-7.18 (m, 3H), 4.77-4.05 (m, 2H), 4.31 (m, 1H), 3.96 (dq, J=7, 3 Hz, 1H), 2.00-1.79 (m, 2H), 1.34 (d, J=7 Hz, 3H). $^{13}$C-NMR: δ 176.1, 151.1, 142.2, 127.7, 125.6, 125.0, 116.2, 110.0, 82.0, 80.4, 68.0, 43.8, 34.7, 34.5, 10.4.

EXAMPLE 3

(±)-(2R*,3S*)-5-fluoro-3-hydroxy-2-methylpentanoyl N-propionylcysteamine thioester A 25% (w/v) solution of sodium methoxide in methanol (22 mL) was added to a stirred solution of N,S-dipropionylcysteamine (18.9 g, 0.1 mol) in 100 mL of methanol at ambient temperature maintained under inert atmosphere. After 15 minutes, acetic acid (4.0 mL) was added, followed by solid N-[(2R*,3S*)-5-fluoro-3-hydroxy-2-methylpentanoyl]-2-benzoxazolone (26.7 g, 0.1 mol). The mixture was stirred for 15 minutes after complete dissolution of the solid is noted, then acetic acid (1.7 mL) was added and the mixture was evaporated under vacuum to yield a thick oil. The oil was dissolved in 500 mL of ethyl acetate and washed once with 500 mL of water. The organic phase was washed once with 250 mL of saturated aq. NaCl, then dried over MgSO$_4$, filtered, and evaporated on the rotary evaporator to yield a thick yellow oil. The residue was dissolved in a minimal volume of dichloromethane and applied to a 100-gm column of silica gel. The column was washed with 2:1 hexanes/ethyl acetate to elute 2-benzoxazolone. The product was eluted with 1:4 hexanes/ethyl acetate, and was evaporated under vacuum to a yellow oil. The oily product was mixed with 100 mL of heptane and heated to 55° C., then the resulting two-phase mixture was allowed to cool to ambient temperature with vigorous stirring. The resulting white solid was collected by filtration and dried under vacuum, giving 24 g of product, mp 42-43° C.

EXAMPLE 4

15-fluoro-6-deoxyerythronolide B ("15F-6dEB")

Analytical methods: 15F-6dEB and overall diketide (combined enantiomers) were determined by HPLC. Samples of whole broth were diluted with methanol four-fold, then clarified by filtration or centrifugation prior to analysis. Aliquots of 10 μL were injected onto an Inertsil ODS3 5 μm column, 150×4.6 (Varian), then eluted using an acetonitrile/water gradient (Table 1) with a flow rate of 1 mL/min at 50° C. 15F-6dEB was detected by ELSD (SEDEX model 55) and total diketide was detected by UV at 250 nm. Under these conditions 15F-6dEB eluted at 9.5 minutes and diketide eluted at 7.3 minutes.

TABLE 1

Solvent gradient program for 15F-6dEB method

| Time (min) | % Acetonitrile | % Water |
|---|---|---|
| 0 | 0 | 100 |
| 2 | 0 | 100 |
| 8 | 100 | 0 |
| 9 | 100 | 0 |
| 9.1 | 0 | 100 |
| 12 | 0 | 100 |

Culture media formulation and preparation: SC-VM6-1 medium supplemented with thiostrepton and apramycin was used for seed cultures (Table 2). Flask medium was autoclaved in 1L bottles for 90 minutes at 121° C. Fermenter medium was sterilized in place for 45 minutes at 121° C. Ten liter seed fermenters were autoclaved empty and then filled by transferring sterile medium from a 150 L fermenter. Thiostrepton was prepared as a 50 g/L stock solution in DMSO, filter sterilized, and added to sterile medium. Apramycin sulfate was prepared as a 50 g/L stock solution in DI water, filter sterilized, and added to sterile medium.

TABLE 2

SC-VM6-1 medium supplemented with thiostrepton and apramycin

| Component | Vendor | Concentration (g/L) |
|---|---|---|
| Corn Starch | Sigma | 45 |
| Corn Steep Liquor | Sigma | 10 |
| Brewer's yeast | Sigma | 10 |
| CaCO$_3$ | EM Science | 1 |
| Glycerol | Alfa Aesar | 8 |
| Antifoam B[1] | JT Baker | 5 |
| HEPES, free acid[2] | Sigma | 23.8 |
| Thiostrepton[3] | Calbiochem | 50 mg/L |
| Apramycin Sulfate[3] | Sigma | 50 mg/L |

[1] use only 1 mL/L Antifoam B for flask medium
[2] add HEPES only for flask medium
[3] added after heat sterilization SC-FM6-3F medium was used for production cultures (Table 3). Fermenter medium was sterilized in place for 45 minutes at 121° C.

TABLE 3

SC-FM6-3F medium

| Component | Vendor | Concentration (g/L) |
|---|---|---|
| Corn Starch | Sigma | 45 |
| Tastone 310 | Sensient | 10 |
| Brewer's yeast | Sigma | 30 |
| CaCO3 | EM Science | 1 |
| Dextrin (C*Dry MD 01956) | Cerestar (Cargill) | 30 |
| Antifoam B (mL) | JT Baker | 5 |

Seed culture preparation: A cell bank (WCB K388-148) of *Streptomyces coelicolor* K460-2 was used to initiate all seed cultures. This strain is a derivative of *Streptomyces coelicolor* CH999 comprising plasmids pKOS279-7A and pKOS146-145 encoding genes for modules 2-6 of 6-deoxyerythronolide B synthase, and requires all seed media to be supplemented with thiostrepton and apramycin. Construction of this strain is described in Ward et al., "Precursor-directed biosynthesis of 6-deoxyerythronolide B analogues is improved by removal of the initial catalytic sitd of polyketide synthase," *J. Ind. Microbiol. Biotechnol.*, (2006), which is incorporated herein by reference, and is detailed below in Example 29. Growth period and volumes of seed culture stages are summarized in Table 4.

TABLE 4

Seed culture stages for 15F-6dEB fermentation

| Seed stage | Medium volume | Vessel type | Inoculum | Growth period |
|---|---|---|---|---|
| 1 | 50 mL | 250 mL baffled flask | Frozen 1 mL stock | 3 days |
| 2 | 500 mL | Baffled Fernbach flask | 50 mL stage 1 culture | 2 days |
| 3 | 8 L | 10 L fermenter | 800 mL stage 2 culture (from two flasks) | 1 day |
| 4 | 80 L | 150 L fermenter | 8.8 L stage 3 culture | 1 day |

Incubation temperature for all seed cultures was 30° C. All shake flasks were shaken at 250 rpm. Fermenter cultures were maintained at pH 6.5 via automated addition of 2.5 NH$_2$SO$_4$ or 2.5 N NaOH. Dissolved oxygen set point in fermenters was 40% and controlled through agitation speed; both 10 L and 150 L fermenters were constrained to 300 rpm minimum and 600 rpm maximum agitation rate. Antifoam B (50%) was added automatically as needed to fermenter cultures.

Production culture operation: The prepared seed culture (ca. 90 L) was sufficient to inoculate both F1000 and F1100. Each production fermenter containing about 750 L SC-FM6-3F medium was inoculated by aseptic transfer of 38 L seed culture. Incubation temperature for production cultures was 30° C. Cultures were maintained at pH 6.5 via automated addition of 2.5 N H$_2$SO$_4$ or 2.5 N NaOH. Dissolved oxygen set point was 40% and controlled using stir rate as cascade #1 (minimum 150 rpm, maximum 300 rpm) and airflow rate as cascade #2 (minimum 50 Lpm, maximum 800 Lpm). Antifoam B (50%) was added automatically as needed. A bolus feed of 2/L of (±)-(2R*,3S*)-5-fluoro-3-hydroxy-2-methyl-pentanoyl N-propionylcysteamine thioester (prepared as a filter-sterilized solution in DMSO at 400 g/kg) was delivered after two days of growth, followed by a second bolus feed of 1 g/L after four days of growth for a total of 3 g/L diketide thioester feeding. Fermentation titers reached 0.94-1.2 g/L in eight to nine days. Harvest was initiated 8-9 days after inoculation.

Primary recovery: Broth was filtered using rotary vacuum drum filtration. Prior to the filtration process, 150 lb. Celite Hyflo (Celite Corp.) was mixed into the broth followed by 4.8 L Cysep 349 (Cytec Inc.) diluted to 10 L with deionized ("DI") water. A precoat of Celite hyflo was applied to the WesTech rotary vacuum drum filter (equipment number M2) by recirculating a slurry of 11 kg of Celite Hyflo in 50 L DI water with vacuum until the maximum precoat thickness (ca. 2 inches) was attained. Filtration was then initiated with the typical conditions as follows: drum speed setting 4; knife indexing setting 3; agitator setting 5; vacuum 26 inches Hg; cake wash water rate 2 L/min. Antifoam B (25%) was added to the filtrate receiver tank as needed (typically 200-500 mL). The filtrate was pumped through a polishing filter (Cuno Zeta Plus part no. 4516704 10M02) before collecting in tanks. Typical yield of product in filtrates was 95 percent with the remainder of product in the discarded filter cake.

Capture: 15F-6dEB was captured from the filtrate by using Diaion HP20SS resin (Itochu Chemicals America Inc.) as follows. A column was prepared with sufficient HP20SS resin to achieve a bed height of at least 30 cm and product loading of <16 g 15F-6dEB per L of resin. For the capture operations performed in the purifications described below, 48 L of resin were used in a 450 mm diameter column (30 cm bed height). The operation of the HP20SS capture process is described in Table 5. NF-grade methanol (Mallinckrodt) and deionized water or equivalent solvents are used for all described chromatography procedures. For immediate re-use of the HP20SS column for 15F-6dEB capture, the resin is washed and equilibrated with 4 column volumes (CV) of water prior to filtrate loading and the capture operation is repeated.

TABLE 5

HP20SS capture operation details

| Column Step | Solvent/Stream | Volume | Flowrate |
|---|---|---|---|
| Equilibration | water | 3-4 CV | 215 cm/hr (5.7 LPM*) |
| 15F-6dEB Load | broth filtrate | NA | 215 cm/hr (5.7 LPM*) |
| Wash1 | water | 2 CV | 215 cm/hr (5.7 LPM*) |
| Wash2 | 30% (v/v) MeOH | 2.4 CV | 150 cm/hr (3.9 LPM*) |
| Wash3 | 50% (v/v) MeOH | 2.4 CV | 150 cm/hr (3.9 LPM*) |
| Elution | 70% (v/v) MeOH | 4.5 CV | 150 cm/hr (3.9 LPM*) |
| Strip | 100% MeOH | 2 CV | 150 cm/hr (3.9 LPM*) |

*Using a 450 mm diameter column

After completion of the capture operation, the HP20SS resin was cleaned by washing with 3 CV of 50% (v/v) MeOH/water with 0.05 N NaOH at 60-120 cm/hr (1.5-3 LPM). Next, the resin was washed with at least 5 CV of water at 60-120 cm/hr until the effluent was at pH 6-8. Finally, the resin was washed with 2 CV of 100% MeOH and stored for later use.

The capture operation serves to isolate product from broth filtrate and to generate material of sufficient purity for bioconversion by fermentation. The majority of fermentation components were removed in the filtrate flow-through or wash eluates. The residual diketide was also removed during the wash steps. The majority of 15F-6dEB eluted from 0.4-3.5 CV of the elution solvent. The capture operation typically achieved >75% purity with a recovery yield of >85%.

Solvent Exchange: The product pool from the capture operation was diluted with water to 25% (v/v) MeOH/water. A column was prepared with sufficient Bakerbond C18 40 μm resin (J. T. Baker) to achieve a bed height of at least 20 cm and product loading of <55 g 15F-6dEB per L of resin. For the solvent exchange operations performed in the purifications described below, 38 L of resin were used in a 440 mm diameter column (25 cm bed height). The column was equilibrated with 4 column volumes ("CV") of 25% (v/v) MeOH/water at 175 cm/hr (4.5 liters per minute (LPM)). Next, the diluted product pool was loaded onto the column at 175 cm/hr. The product was eluted with 2-3 CV of 100% non-denatured ethanol (Goldshield Distributors) at a flow rate of 100 cm/hr (2.5 LPM). 15F-6dEB typically elutes from 0.75-1.75 CV and elution fractions were pooled to achieve >95% recovery. Elution of 15F-6dEB can be monitored online by UV absorbance at 254 nm. After completion of the solvent exchange operation, the resin was cleaned by washing with 3 CV of 80% (v/v) MeOH/20% (v/v) 50 mM Tris pH 7.8. The resin was then washed with 2 CV of 100% MeOH and stored for later use.

Vacuum Distillation and Filtration Operations: The solvent exchange eluate containing the 15F-6dEB was further concentrated by vacuum distillation and filtered to prepare the 15F-6dEB solution for bioconversion. Vacuum distillation was carried out using a R-220 Buchi Rotavapor System (Buchi Labs, Switzerland) with a 20L flask or equivalent apparatus. The rotavapor system was operated with waterbath at 40° C., chiller at <5° C., vapor at <20° C., vacuum at 50-90 mBar, and agitation at 60-120 rpm. The solvent exchange eluate was distilled until a product concentration of >150 g/L 15F-6dEB was achieved. Next, the concentrated product pool was filtered (Pall HDC II 1.2 μm nominal PP filter cartridge or equivalent) to remove insolubles. Additional 100% ethanol was used to rinse equipment and washed through the filtration apparatus to dilute the filtered product pool to >100 g/L 15F-6dEB. This filtered pool was then ready for sterilization with an appropriate filter and feeding to the bioconversion fermentation.

Characterization: A sample of crude 15-F-6dEB was purified by chromatography on silica gel using a gradient of hexanes and ethyl acetate. Fractions containing the product were pooled and concentrated to a pale yellow oil that spontaneously crystallized. Recrystallization from ether-hexane gave pure 15-fluoro-6-deoxyerythronolide B. APCI-MS: m/z 405 ([M+H]$^+$). $^{19}$F-NMR (CDCl$_3$, 376 MHz): δ −222.0 (relative to CF$_3$CO$_2$H at δ −77.0). $^1$H-NMR (CDCl$_3$, 400 MHz): δ 5.49 (m, 1H); 4.94 (m, 2H); 3.99 (m, 1H); 3.90 (d, 1H, J=10); 3.84 (d, 1H, J=4); 3.70 (m, 1H); 3.18 (br s, 1H); 2.79 (m, 1H); 2.77 (m, 1H); 2.61 (m, 1H); 2.47 (br s, 1H); 2.20 (m, 1H); 2.00 (m, 1H); 1.92 (m, 1H); 1.85 (m, 1H); 1.70 (m, 1H); 1.65 (dd, 1H, J=4, 10); 1.29 (d, 3H, J=7); 1.24 (dd, 1H, J=4, 10); 1.07 (d, 3H, J=7); 1.06 (d, 3H, J=7); 1.05 (d, 3H, J=7); 1.02 (d, 3H, J=7); 0.93 (d, 3H, J=7). $^{13}$C-NMR (CDCl$_3$, 100 MHz): δ 213.70, 177.98, 80.68 (d, J$_{CF}$=167 Hz), 79.34, 76.37, 70.84 (d, J$_{CF}$=4 Hz), 70.74, 43.88, 43.27, 41.13, 39.54, 37.63, 37.52, 35.52, 33.34 (d, J$_{CF}$=20 Hz), 16.63, 14.60, 13.32, 9.20, 6.92, 6.28.

EXAMPLE 5

15-fluoroerythromycin A ("15F-EryA")

Analytical methods: Filtrate samples were analyzed for 15F-EryA using a HPLC equipped with an evaporative light scattering detector (ELSD). Samples of filtrate were diluted four-fold with methanol (MeOH) and then were clarified by filtration. Aliquots of 10 μL of filtered sample were injected onto a guard column (4.6 mm×10 mm Metasil Basic 5 μm, Varian) and main column (4.6 mm×250 mm Metasil Basic 5 μm, Varian) held at 50° C. 15F-EryA was resolved using an isocratic method (1 mL/min flowrate) consisting of 55% organic (4:1 acetonitrile:20 mM ammonium acetate in methanol) mixture and 45% 5 mM ammonium acetate in water. 15F-EryA eluted at 5.0 min and was quantitated using a standard curve (100-500 mg/L 15F-EryA) fitted with a power function (Y=aX$^b$) that was generated each time samples are analyzed.

In-process purification samples were analyzed for 15F-EryA using a HPLC equipped with a UV detector. Samples were diluted appropriately (1-5 g/L 15F-EryA) in methanol and 10 μL was injected onto a Phenomenex Luna C18(2) 5 μm 250 mm×4.6 mm column held at 40° C. 15F-EryA was resolved using an isocratic method with mobile phase (40:55:5 20 mM sodium phosphate pH 8 buffer:acetonitrile:methanol) at 1.25 mL/min and was detected by UV absorbance at 210 nm. Under these conditions, 15F-EryA elutes at 5.9 min and was quantitated using a linear fit (Y=aX+b) of standards (0.34 g/L and 2 g/L). Typical measurement uncertainty was <5%.

The total solids concentration in purification pools is determined by drying 5-10 mL of solution in a moisture balance to constant weight. Total solids concentration was used to estimate in-process purity as 15F-EryA concentration divided by solids concentration.

15F-6dEB precursor: 15F-6dEB (>85% purity) was produced as described in Example 4 above. The 15F-6dEB was dissolved in ethanol to yield a solution of 193 g/kg 15F-6dEB. This solution was filter sterilized before being fed to the fermentation.

Culture media formulation and preparation: SE-VI medium supplemented with apramycin was used for seed cultures (Table 6). Flask medium was autoclaved in 1 L bottles for 90 minutes at 121° C. Fermenter medium was sterilized in place for 45 minutes at 121° C. Ten liter seed fermenters were autoclaved empty and then filled by transferring sterile medium from a 150 L fermenter. Apramycin sulfate was prepared as a 50 g/L stock solution in DI water, filter sterilized, and added to sterile medium. SE-F2 medium was used for production cultures (Table 7). Fermenter medium was sterilized in place for 45 minutes at 121° C.

TABLE 6

SE-V1 medium supplemented with apramycin

| Component | Vendor | Concentration (g/L) |
|---|---|---|
| Corn Starch | Sigma | 16.0 |
| Corn Dextrin | Sigma | 10.0 |
| Soya Meal Flour | Giusto's | 15.0 |
| Sodium Chloride | Sigma | 2.5 |
| Corn Steep Powder | Marcor | 2.5 |
| Ammonium Sulfate | Sigma | 1.0 |
| Soy Bean Oil | Sigma | 6.0 |
| Calcium Carbonate | EM Science | 4.0 |
| Antifoam B | JT Baker | 5.0 (mL/L) |
| Apramycin Sulfate[1] | Sigma | 30 mg/L |

[1] added after heat sterilization

TABLE 7

SE-F2 medium

| Component | Vendor | Concentration (g/L) |
|---|---|---|
| Corn Starch | Sigma | 28.0 |
| Soya Meal Flour | Giusto's | 24.0 |
| Sodium Chloride | Sigma, JT Baker | 5.5 |
| Corn Steep Powder | Marcor | 4.0 |
| Ammonium Sulfate | Sigma | 1.5 |
| Soy Bean Oil | Sigma | 4.5 |
| Calcium Carbonate | EM Science, Spectrum | 6.0 |
| Antifoam B | JT Baker | 5.0 |

Nutrient feeds: Two nutrient feeds were prepared for the production fermentation: soy oil (Sigma) was filter sterilized prior to feeding, and 300 g/kg corn dextrin (Sigma, part #D-2256) was sterilized in place for 45 minutes at 121° C.

Seed culture preparation: *Saccharopolyspora erythraea* strain K301-105B, cell bank WCB K479-042 was used to initiate all seed cultures. This strain requires all seed media to be supplemented with apramycin. Growth period and volumes of seed culture stages are summarized in Table 8.

TABLE 8

Seed culture stages for 15F-EryA fermentation

| Seed stage | Medium volume | Vessel type | Inoculum | Growth period |
|---|---|---|---|---|
| 1 | 50 mL | 250 mL baffled flask | Frozen 1 mL stock | 2 days |
| 2 | 500 mL | Baffled Fernbach flask | 50 mL stage 1 culture | 2 days |
| 3 | 8 L | 10 L fermenter | 800 mL stage 2 culture (from two flasks) | 1 day[1] |
| 4 | 80 L | 150 L fermenter | 8.8 L stage 3 culture | 1 day |

[1] can be extended by 1 day if cell growth is slow

Incubation temperature for all seed cultures was 34° C. All shake flasks were shaken at 250 rpm. Fermenter cultures were maintained at pH 7.0 via automated addition of 2.5 $NH_2SO_4$ or 2.5 N NaOH. Dissolved oxygen set point in fermenters was 40% and controlled through agitation speed; both 10 L and 150 L fermenters were constrained to 300 rpm minimum and 600 rpm maximum agitation rate. Antifoam B (50%) was added automatically as needed to fermenter cultures.

Production culture operation: The prepared seed culture (ca. 90 L) was sufficient to inoculate two large-scale fermenters. Each production fermenter containing approximately 600 L SE-F2 medium was inoculated by aseptic transfer of 30 L seed culture. The total amount of 15F-6dEB fed to each fermenter (ca. 1 kg) was based on anticipated bioconversion yield and the known loading capacity of downstream processes. A reduced medium volume (600 L) provided sufficient bioconversion capacity while simplifying downstream processing. Process value set points as well as precursor and nutrient feed parameters are summarized in Table 9. Fermentation titers reached 2.0-2.3 g/L in five to six days. The molar yield of 15F-EryA from 15F-6dEB was 76%-82%.

TABLE 9

Production fermentation process set points and feed parameters

| Time point | Parameter or event |
|---|---|
| 0 hr | Temperature = 34° C. |
| | pH = 7.0, using 2.5 N $H_2SO_4$ and 2.5 N NaOH |
| | pressure = 300 mB |
| | DO set point = 40% |
| | $1^{st}$ cascade = stir, min 200, max 375 rpm |
| | $2^{nd}$ cascade = airflow, min 130, max 800 L/min |
| | Foam control using 50% Antifoam B |
| 24 hr | Increase vessel pressure; new pressure = 500 mB |
| | Increase DO set point; new DO set point = 75% |
| | Start soy oil feed; feed rate = 2.3 g/L/d |
| | Start 300 g/kg corn dextrin feed; feed rate = 27 g/L/d |
| | Deliver initial 15F-6dEB feed (350 mg/L) |
| | Start continuous 15F-6dEB feed (350 mg/L/d) |
| 48 hr | Increase soy oil feed rate; new feed rate = 4.6 g/L/d (maintain until end of fermentation) |
| 96 hr | Stop 300 g/kg corn dextrin feed |
| | Stop 15F-6dEB feed |

Primary recovery: Broth was harvested at 5-6 days and was filtered using rotary vacuum drum filtration. Prior to the filtration process, 100 lb of Celite Hyflo (Celite Corp.) was mixed into the broth followed by 1.4 L Cysep 349 (Cytec Inc.) diluted to 10 L with DI water. A precoat of Celite hyflo was applied to the WesTech rotary vacuum drum filter (equipment number M2) by recirculating a slurry of 11 kg Celite Hyflo in 50 L DI water with vacuum until the maximum precoat thickness (ca. 2 inches) was attained. Filtration was then initiated with the typical conditions as follows: drum speed setting 4; knife indexing setting 3; agitator setting 5; vacuum 26 inches Hg; cake wash water rate 2 L/min. Antifoam B (25%) was added to the filtrate receiver tank as needed (typically 100-300 mL). The filtrate was pumped through a polishing filter (Cuno Zeta Plus part no. 4516704 10M02) before collecting in tanks. Typical yield of product in filtrates was 95 percent with the remainder of product in the discarded filter cake.

Capture: 15F-EryA was captured from the above-described filtrate using Diaion HP20SS resin (Itochu Chemicals America Inc.) as follows. A column was prepared with sufficient HP20SS resin to achieve a bed height of at least 26 cm and product loading of <15 g 15F-EryA per L of resin. For the purifications described below, 40-48 L of resin were used in 450 mm diameter columns (26-31 cm bed height). The operation of the HP20SS capture process is described in Table 10. NF-grade methanol (Mallinckrodt) and deionized (DI) water or equivalent solvents were used for all described chromatography procedures. For immediate re-use of the HP20SS column for 15F-EryA capture, the resin is washed and equilibrated with 4 column volumes (CV) of water prior to filtrate loading and the capture operation is repeated.

After completion of the capture operation, the HP20SS resin is cleaned by washing with 3 CV of 50% (v/v) MeOH/water with 0.05 N NaOH at 60-120 cm/hr (1.5-3 LPM). Next, the resin is washed with at least 5 CV of water at 60-120 cm/hr until the effluent is at pH 6-8. Finally, the resin is washed with 2 CV of 100% MeOH and stored for later use.

TABLE 10

| HP20SS capture operation details | | | |
| --- | --- | --- | --- |
| Column Step | Solvent/Stream | Volume | Flowrate |
| Equilibration | water | 3-4 CV | 215 cm/hr (5.7 LPM*) |
| 15F-EryA Load | broth filtrate | NA | 150 cm/hr (3.9 LPM*) |
| Wash1 | water | 2 CV | 150 cm/hr (3.9 LPM*) |
| Wash2 | 30% (v/v) MeOH | 2 CV | 150 cm/hr (3.9 LPM*) |
| Wash3 | 50% (v/v) MeOH | 1.8 CV | 125 cm/hr (3.3 LPM*) |
| Elution | 100% MeOH | 2.5 CV | 125 cm/hr (3.3 LPM*) |

*Using a 450 mm diameter column

Vacuum Distillation: The product pool from the capture operation was concentrated by vacuum distillation to remove MeOH. Vacuum distillation was carried out using a R-220 Buchi Rotavapor System (Buchi Labs, Switzerland) with a 20L flask or equivalent apparatus. The rotavapor system was initially operated with waterbath at 40-50° C., chiller at <0° C., vapor at 18-22° C., vacuum at 50-90 mBar, and agitation at 60-120 rpm. The vacuum pressure setting was manually controlled to maintain a vapor temperature of 18-22° C. The distillation was considered complete when the pool volume had been reduced by ~90% and the MeOH content was sufficiently low to proceed with the subsequent extraction operation.

Liquid-Liquid Extraction: The concentrated capture pool was transferred to a suitable container to perform liquid-liquid extraction with ethyl acetate (EtOAc). A saturated solution of sodium bicarbonate was added (at least two-fold dilution) to a final volume of 26 L per 800 L of harvested broth. This aqueous pool, or feed, was verified to be at pH 8-9 before extraction. The pH may be adjusted up to pH 8 with sodium hydroxide if necessary. The feed was extracted by adding ⅓ volume of ethyl acetate ("EtOAc") and agitating gently for 2 minutes (i.e. agitating at the minimum rate that the mixture visually appeared well-mixed). The extraction mixture was allowed to settle until phases separated (typically 1-2 hrs with organic extract on top of aqueous raffinate). The EtOAc extract was transferred to a new container. The extraction was repeated twice with ⅓ volume of EtOAc and adjustment of raffinate to pH 8-9 prior to each extraction, if necessary. The organic extracts were combined and extracted sequentially with ⅓ volume saturated sodium bicarbonate in water and ⅓ volume saturated sodium chloride in water.

Drying: The organic pool from the liquid-liquid extraction was dried to solids to remove all solvent. The organic pool was dried to solids in a R-220 Buchi Rotavapor System with a 20 L flask. The rotavapor system was operated with water-bath at 40° C., chiller at <0° C., vapor at 18-22° C., vacuum at 50-110 mBar, and agitation at 60-120 rpm. The vacuum pressure setting was manually controlled to maintain a vapor temperature of 18-22° C. The solids are broken up and further dried to constant weight in a vacuum oven at 40° C. and 5-30 mBar.

Crystallization: High purity 15F-EryA was produced by crystallization of the product from a MeOH/water solvent system. The following procedure used HPLC-grade MeOH and water. The dried extraction solids were dissolved by adding 4 L of MeOH per 1 kg of 15F-EryA and mixing gently (e.g., 60 rpm in a 20L flask in rotavapor system) for 30-45 min. The solution was filtered with a 0.2 μm PVDF membrane (Millipore Millipak-100 Gamma Gold or equivalent) to remove fine particulates. The filtered solids are washed with an additional 1 L of MeOH per 1 kg of 15F-Ery A and the combined filtrates are transferred to a suitable crystallization vessel capable of sufficient agitation to maintain a well-mixed system. The starting material solids added ~1 L of volume per 1 kg of 15F-Ery A to bring the initial crystallization solution to 6 L per 1 kg of 15F-Ery A. The crystallization was started by adding 3.33 L of water per 1 kg of 15F-Ery A over 60 min (55.6 mL/min) to achieve a 6:4 MeOH/water ratio. Crystal formation was initiated by adding a seed crystal slurry (0.5 g 15F-EryA crystals in 5 mL of 30% (v/v) MeOH) and holding for 1 hr. Initiation of crystallization was assessed by visual observation of increased turbidity. After the hold time, 8.33 L of water per 1 kg of 15F-Ery A were added over 4 hrs (34.7 mL/min) to achieve the final 3:7 MeOH/water ratio. The crystallization proceeded to completion over the next 12-16 hrs. The high purity 15F-EryA crystals were harvested by filtration (Whatman#2 filter paper or equivalent) and the filtrate collected as the mother liquor. The filtered crystals were washed with 2 L of 30% (v/v) MeOH and the filtrate was collected as the crystal wash. The washed crystals were transferred to a drying container and dried in a vacuum oven (40° C. and 5-20 mBar) to constant weight. The dried crystals were transferred to a new container as the final product. The crystallizer and all equipment were rinsed with 100% MeOH to remove residual product and collected as the equipment rinse. The crystallization of two batches resulted in 79% and 84% yield, respectively, of crystals of >90% purity as determined by HPLC assay, $^1$H-NMR, and $^{13}$C-NMR. The purification of the two combined large-scale fermentations resulted in a combined amount of 1.9 kg of high purity 15F-EryA.

EXAMPLE 6

15-fluoroerythromycin A 9-(E)-oxime

A 50% aqueous solution of hydroxylamine (750 mL) was added to a mixture of 15-fluoro-erythromycin A (750 g), isopropanol (2000 mL), and acetic acid (250 mL), and the resulting solution was warmed to 50° C. and stirred for 19.5 hours. The mixture was cooled on ice and treated with a solution of KOH (240 g) in water (1000 mL), maintaining the temperature below 30° C. The resulting mixture was extracted twice with 1000 mL of ethyl acetate. The organic extracts were combined, washed sequentially with water (1000 mL), sat. aq. NaHCO$_3$ (500 mL), and twice with brine (500 mL), then dried over MgSO$_4$, filtered, and evaporated in vacuo. Methanol (250 mL) was added to dissolve the residue, then 2000 mL of hexanes was added and the mixture was evaporated to dryness in vacuo; this step was repeated. The residue was purified by crystallization from methanol/CH$_2$Cl$_2$ to provide 15-fluoroerythromycin A 9-(E)-oxime (613 g). LC-MS: m/z 767.5 [M+H]$^+$. $^{13}$C-NMR (CD$_3$OD): δ 174.8, 169.7, 102.5, 96.1, 82.3 (d, J$_{CF}$=162 Hz), 82.6, 78.9, 77.8, 74.8, 74.4, 73.1, 71.8, 71.1, 70.5, 67.4, 65.3, 65.0, 49.3, 44.6, 40.7 (2C), 38.1, 35.4, 30.3, 29.6 (d, J$_{CF}$=18 Hz), 27.0, 25.6, 21.9, 21.3, 19.1 (3C), 17.4, 15.9, 14.9, 9.6.

EXAMPLE 7

15-fluoroerythromycin A 9-oxime 2',4",9-tri-O-benzoate

A mixture of 15-fluoroerythromycin A 9-(E)-oxime (503 g) and benzoic anhydride (668 g) was dissolved in anhydrous tetrahydrofuran (5.4 L), and triethylamine (488 mL) was added followed by 4-(dimethylamino)pyridine (80 g). The mixture was stirred at ambient temperature for 40 hours, then cooled on ice and treated with N,N-dimethylethylenediamine (130 mL) at such a rate as to keep the internal temperature below 10° C. The solution was stirred for an additional 40 minutes, then poured into methyl tert-butyl ether (5.5 L) and washed twice with 5% w/v aqueous KH$_2$PO$_4$ (5 L). The organic phase was further washed sequentially with sat. aq. NaHCO$_3$ (4 L) and brine (2 L), then dried over MgSO$_4$, filtered, and evaporated in vacuo. The crude product was crystallized from isopropanol (3 L), yielding 570 g of product. LC-MS: m/z 1079.5 [M+H]$^+$. $^{13}$C-NMR (CDCl$_3$): δ 179.3, 174.8, 166.0, 165.4, 163.8, 133.2 (2C), 132.6, 130.7, 129.9, 129.6, 129.5, 129.4, 128.9, 128.5, 128.3, 128.2, 100.2, 95.7, 83.5, 82.5 (d, J$_{CF}$=170 Hz), 79.0, 78.8, 74.7, 73.9, 72.9, 72.5 (d, J$_{CF}$=4 Hz), 72.3, 69.3, 67.7, 63.7, 63.4, 49.5, 44.3, 40.8 (2C), 35.3, 34.5, 31.6, 29.4 (d, J$_{CF}$=20 Hz), 28.6, 21.2, 18.4, 18.2, 16.4, 15.0, 14.7, 9.3.

EXAMPLE 8

6-O-allyl-15-fluoroerythromycin A 9-oxime 2',4",9-tri-O-benzoate

A mixture of allyl tert-butyl carbonate (160 mg) and 15-fluoroerythromycin A 9-oxime 2',4",9-tri-O-benzoate (450 mg) was dissolved in anhydrous tetrahydrofuran (2 mL) and sparged with nitrogen for 5 minutes. Tris(dibenzylideneacetone)palladium-chloroform (5 mg) was added, followed by tert-butyl isocyanide (5 μL) and the greenish-brown mixture was heated in an 80° C. bath for 16 hours. The reaction was cooled to ambient temperature and applied to a column of silica gel (120 g) equilibrated in 10% acetone/hexanes+1% Et$_3$N. The column was eluted with a linear gradient from 10% to 50% acetone/hexanes+1% Et$_3$N, and the fractions containing product were pooled and evaporated to dryness, yielding 355 mg of the product as a white powder. MS: m/z 1120 ([M+H$^+$]). $^{13}$C-NMR (100 MHz, CDCl$_3$): δ 177.2, 174.3, 166.1, 165.5, 163.1, 134.4, 133.4, 133.1, 132.6, 130.7, 129.8, 129.6, 129.3, 129.2, 128.6, 128.4, 128.2, 117.2, 99.7, 96.2, 83.3, 82.5 (d, J$_{CF}$=165 Hz), 79.1, 79.0, 78.7, 78.3, 73.7, 72.9, 72.8, 72.6, 69.0, 67.2, 65.6, 63.7, 63.6, 49.5, 44.1, 40.8 (2C), 37.7, 36.6, 35.3, 34.3, 31.6, 30.9, 29.5 (d, J$_{CF}$=20 Hz), 28.6, 21.3, 21.2, 18.9, 18.5, 16.5, 15.3, 15.1, 9.5.

EXAMPLE 9

6-O-allyl-15-fluoroerythromycin A 9-oxime 2',4"-di-O-benzoate

6-O-allyl-15-fluoroerythromycin A 9-oxime 2',4",9-tri-O-benzoate (crude product from allylation of 15-fluoroerythromycin A 9-oxime 2',4",9-tri-O-benzoate, 482 mmol) was dissolved in a mixture of tetrahydrofuran (1 L) and isopropanol (1.5 L) and cooled to 12° C., then treated with 1 M NaOH (526 mL) for 90 minutes. The solution was partitioned between methyl tert-butyl ether (4 L) and sat. aq. NaHCO$_3$ (3 L). The aqueous phase was extracted twice with methyl tert-butyl ether (2 L), and the organic extracts were combined, dried with MgSO$_4$, filtered, and evaporated to dryness to provide 524 g of the product. LC-MS: m/z=1015.6 [M+H]$^+$. $^{13}$C-NMR (100 MHz, CDCl$_3$): δ 174.6, 169.8, 166.1, 165.4, 136.3, 133.3, 132.6, 130.8, 129.8, 129.6, 128.4, 128.2, 115.9, 99.8, 96.1, 82.5 (d, J$_{CF}$=164 Hz), 79.3, 79.2, 78.8, 78.4, 73.6, 72.9, 72.5, 69.5, 67.2, 65.6, 63.6, 49.5, 44.2, 40.9 (2C), 38.1, 36.2, 35.3, 32.8, 31.8, 29.6 (d, J$_{CF}$=19 Hz), 25.3, 21.9, 21.2, 21.1, 18.8, 18.4, 16.3, 15.3, 14.8, 9.4.

EXAMPLE 10

6-O-allyl-15-fluoroerythromycin A 2',4"-di-O-benzoate

To a solution of 524 g of 6-O-allyl-15-fluoroerythromycin A 9-oxime 2',4"-di-O-benzoate in ethanol (2 L) was added water (2 L) followed by sodium hydrosulfite (732 g). The mixture was degassed for 20 minutes by sparging with nitrogen. Formic acid (192 mL) was added and the resulting mixture was stirred at 80° C. for 2.5 hours. After cooling, the mixture was concentrated in vacuo to remove the ethanol and the residue was partitioned between EtOAc (3 L) and sat. aq. NaHCO$_3$ (2 L). The aqueous phase was extracted twice with EtOAc (2 L). The combined organics were dried (MgSO$_4$), filtered, and concentrated under reduced pressure. The residue was dissolved in acetone (200 mL), diluted with hexane (800 mL), and mixed with 200 g of silica gel. The resulting slurry was placed on a column of silica gel (550 g) packed with 20% acetone/hexanes containing 1% Et$_3$N. The column was eluted with 20% acetone/hexanes containing 1% Et$_3$N, and fractions containing product were combined and concentrated in vacuo to provide 514 g of residue. The residue was crystallized from 514 mL of ethanol to provide 304 g of pure product. The mother liquors were concentrated to yield 150 g of residue, which was chromatographed as described above using 792 g of silica gel to provide an additional 102 g of product. LC-MS: m/z=1000.6 [M+H]$^+$. $^{13}$C-NMR (CDCl$_3$): δ 219.9, 174.6, 166.1, 165.4, 135.6, 133.3, 132.6, 130.8, 129.8, 129.6, 128.3, 128.2, 117.0, 99.8, 96.1, 82.5 (d, J$_{CF}$=164 Hz), 79.9, 79.1, 78.8, 78.3, 73.9, 72.9, 72.5, 72.3 (br), 68.0, 67.3, 65.7, 63.7, 49.5, 45.3, 44.2, 40.9 (2C), 38.0, 37.6, 37.3, 35.3, 31.6, 29.4 (d, J$_{CF}$=19 Hz), 21.5, 21.2, 21.0, 18.5, 18.3, 16.3, 15.3, 12.2, 9.4.

EXAMPLE 11

6-O-allyl-11-amino-11-deoxy-15-fluoroerythromycin A-11,12-cyclic carbamate 2',4"-di-O-benzoate A solution of 6-O-allyl-15-fluoroerythromycin A 2',4"-di-O-benzoate (404 g) and 1,1-carbonyldiimidazole (281.4 g) in tetrahydrofuran (3 L) and dimethylformamide (3 L) was cooled on ice, and sodium hydride (23.3 g) was added in portions to control foaming and to keep the internal temperature below 10° C. The mixture was warmed to ambient temperature and stirred for 18 hours. The resulting mixture was fitted with a dry ice condenser and cooled to −15° C. Anhydrous ammonia gas was condensed into the reaction for 90 minutes at a rate of 1.7 L/min, then the mixture was allowed to warm to 15° C. over a period of 6 hours. The dry ice condenser was removed, potassium tert-butoxide (49.7 g) was added, and the mixture was stirred for 17 hours. The solution was poured into 4 L of 5% w/v aqueous $KH_2PO_4$ and extracted twice with methyl tert-butyl ether (4 L). The extracts were combined, washed sequentially with sat. aq. $NaHCO_3$ (4 L), twice with water (4 L), and brine (4 L), then dried over $MgSO_4$, filtered, and evaporated in vacuo. The crude material was dissolved in 160 mL of hot acetone and diluted with 480 mL of hexanes, then allowed to crystallize. The mother liquors were concentrated, then slurried with 150 g of silica gel in 100 mL of acetone and 200 mL of hexanes and chromatographed on silica gel (900 g), eluting with 25% acetone/hexanes. Product-containing fractions were combined and evaporated to provide additional product (total 298 g). LC-MS: m/z=1025.6 $[M+H]^+$. $^{13}$C-NMR ($CDCl_3$): δ 217.5, 175.5, 166.1, 166.3, 157.8, 134.3, 133.3, 132.7, 130.7, 129.6, 129.5, 128.4, 128.2, 118.4, 99.9, 95.9, 83.3, 81.7 (d, $J_{CF}$=165 Hz), 79.3, 79.1, 78.7, 77.7, 72.9, 72.5, 71.8, 67.5, 65.5, 63.6, 63.5, 57.0, 49.5, 45.1, 44.4, 40.8 (2C), 39.1, 37.8, 37.2, 35.1, 31.7, 30.3, 21.2, 21.0, 18.4, 18.3, 14.6, 13.7, 13.4, 9.4.

EXAMPLE 12

6-O-(1-(7-quinolyl)-3-propenyl)-11-amino-11-deoxy-15-fluoroerythromycin A-11,12-cyclic carbamate 2',4''-di-O-benzoate A solution of 6-O-allyl-11-amino-11-deoxy-15-fluoroerythromycin A-11,12-cyclic carbamate 2',4''-di-O-benzoate (295 g), 7-quinolyl triflate (82 g), bis(diphenylphosphino)ferrocene (dppf, 8 g), and N,N-diisopropylethylamine (100 mL) in 1200 mL of anhydrous dimethylformamide was sparged with nitrogen for 15 minutes, then treated with palladium bromide (4 g) and heated at 80° C. for 14 hours. The mixture was cooled and partitioned between ethyl acetate (3 L) and sat. aq. $NaHCO_3$ (3 L). The organic phase was washed twice with water (3 L), and the combined aqueous phases were extracted with ethyl acetate (3 L). The organic phases were combined, dried over $MgSO_4$, filtered, and evaporated in vacuo. The residue was dissolved in 1 L of 50% acetone/hexanes and slurried with 260 g of silica gel. The mixture was then placed on a column of silica gel (670 g) packed with 50% acetone/hexanes+0.1% $Et_3N$. Fractions containing the product were combined and evaporated, yielding 318 g of product. LC-MS: m/z=1152.6 $[M+H]^+$, 576.8 $[M+2H]^{2+}$. $^{13}$C-NMR ($CDCl_3$): δ 217.7, 175.8, 166.1, 165.3, 157.3, 150.5, 148.6, 137.8, 135.7, 133.3, 132.7, 130.7, 129.8, 129.7, 129.6, 128.3, 128.2, 128.0, 127.2, 124.0, 120.7, 100.1, 96.0, 83.0, 81.7 (d, $J_{CF}$=165 Hz), 79.3, 78.7 (2C), 77.9, 73.0, 72.5, 72.1, 67.6, 64.8, 63.7, 63.6, 57.5, 49.6, 45.2, 44.4, 40.8 (2C), 39.4, 37.9, 37.2, 36.4, 35.1, 31.7, 21.3, 21.2, 21.1, 18.5, 18.3, 14.6, 13.6, 13.4, 9.4.

EXAMPLE 13

6-O-(1-(7-quinolyl)-3-propenyl)-11-amino-11-deoxy-3-(descladinosyl)-15-fluoroerythromycin A-11,12-cyclic carbamate 2'-O-benzoate Trifluoroacetic acid (277 mL) was added over 30 minutes to a solution of 6-O-(1-(7-quinolyl)-3-propenyl)-11-amino-11-deoxy-15-fluoroerythromycin A-11,12-cyclic carbamate 2', 4''-di-O-benzoate (318 g) and triethylsilane (132 mL) in 1.4 L of $CH_2Cl_2$. The mixture was stirred for 2.5 hours, then cooled on ice and treated with a solution of NaOH (140 g) in water (2 L), keeping the internal temperature below 20° C. The mixture was partitioned between $CH_2Cl_2$ (2 L) and sat. aq. $NaHCO_3$ (1 L), and the aqueous phase was extracted twice with $CH_2Cl_2$ (2 L). The organic phases were combined, dried over $MgSO_4$, filtered, and evaporated in vacuo. The residue was dissolved in 2 L of acetonitrile and extracted six times with hexanes (2 L), and the acetonitrile phase was concentrated in vacuo. The residue was dissolved in 1 L of 40% acetone/hexanes and mixed with 200 g of silica gel. The slurry was placed on a column of silica gel (880 g) packed with 40% acetone/hexanes+1% $Et_3N$. The column was eluted sequentially with 2 L of 40% acetone/hexanes+1% $Et_3N$ followed by 6 L of 50% acetone/hexanes+1% $Et_3N$. Product-containing fractions were combined and evaporated in vacuo, providing 198 g of product. LC-MS: m/z=890.5 $[M+H]^+$, 445.7 $[M+2H]^{2+}$. $^{13}$C-NMR ($CDCl_3$): δ 217.3, 175.2, 165.4, 157.7, 150.2, 148.2, 138.3, 136.2, 132.7, 132.2, 130.6, 129.8, 128.3, 128.2, 128.0, 127.4, 124.1, 120.8, 99.2, 83.2, 81.7 (d, $J_{CF}$=165 Hz), 80.7, 80.3, 79.0, 72.1, 71.6, 68.9, 64.1, 63.0, 57.8, 45.4, 43.9, 40.8, 38.2, 37.0, 36.1, 32.2, 31,5, 30.3, 30.1, 22.6, 21.0, 20.1, 18.2, 14.7, 14.1, 13.7, 13.4, 8.1.

EXAMPLE 14

6-O-(1-(7-quinolyl)-3-propenyl)-11-amino-11-deoxy-3-(descladinosyl)-3-oxo-15-fluoroerythromycin A-11,12-cyclic carbamate 2'-O-benzoate (compound of formula (I) wherein $R^1$=H and $R^2$=benzoyl)

To a mixture of 44 g of N-chlorosuccinimide in dichloromethane (300 ml) at −15° C. was added 27.5 mL of methyl sulfide over 40 minutes, maintaining the internal temperature below 15° C. After stirring for a further 30 minutes with the internal temperature maintained at −15° C., a precooled (−15° C.) solution of 196 g of 6-O-(1-(7-quinolyl)-3-propenyl)-11-amino-11-deoxy-3-(descladinosyl)-15-fluoroerythromycin A-11,12-cyclic carbamate 2'-O-benzoate in dichloromethane (600 ml) was added via canula. The solution was stirred between −15° C. and −13° C. for 30 minutes before adding 34 mL of triethylamine. The solution was maintained at −10° C. for 20 minutes before warming to room temperature over 90 minutes. The solution was diluted with dichloromethane (500 ml) and washed with saturated aqueous $NaHCO_3$ (1000 ml). The combined aqueous phases were back extracted with $CH_2Cl_2$ (500 ml). The combined organics were washed with brine (1000 ml), dried ($MgSO_4$), filtered, and concentrated under reduced pressure. Column chromatography (silica, 35% acetone-hexane+1% $Et_3N$, then 45% acetone-hexane+1% $Et_3N$) yielded the product (162 g) as a yellow solid. LC-MS: m/z=888.5 $[M+H]^+$, 444.7 $[M+2H]^{2+}$. $^{13}$C-NMR ($CDCl_3$): δ 217.1, 205.3, 169.2, 165.2, 157.1, 150.6, 148.6, 137.7, 135.7, 133.0, 132.8, 130.4, 129.6, 128.2, 128.1, 128.0, 127.5, 123.9, 120.7, 100.7, 82.7, 81.8 (d, $J_{CF}$=165 Hz), 78.6, 75.5, 73.9, 71.9, 69.1, 64.2, 63.4, 57.8, 50.8, 46.1, 45.7, 44.9, 40.7 (2C), 38.5, 37.1, 31.4, 30.2 (d, $J_{CF}$=20 Hz), 21.0, 20.2, 18.0, 14.3, 13.6, 13.5, 13.2, 11.5.

EXAMPLE 15

6-O-(1-(7-quinolyl)-3-propenyl)-11-amino-11-deoxy-3-(descladinosyl)-3-oxo-15-fluoroerythromycin A-11,12-cyclic carbamate (Compound of Formula (II))

A solution of 1.46 g of 6-O-(1-(7-quinolyl)-3-propenyl)-11-amino-11-deoxy-3-(descladinosyl)-3-oxo-15-fluoroerythromycin A-11,12-cyclic carbamate 2'-O-benzoate in 20 mL of methanol was heated at 50° C. for 16 hours, then cooled and evaporated to dryness in vacuo. Chromatography on silica gel (linear gradient from 10% acetone to 80% acetone in hexanes+1% $Et_3N$) yielded the product, which was crystallized from 1:1 acetone/hexanes. $^{13}$C-NMR (CDCl$_3$): δ 217.1, 205.2, 169.3, 157.1, 150.5, 148.6, 137.8, 135.7, 133.0, 128.1, 127.9, 127.6, 124.0, 120.7, 102.9, 82.8, 81.7 (d, $J_{CF}$=166 Hz), 78.6, 73.8, 70.2, 69.5, 65.8, 64.3, 57.8, 50.9, 46.3, 45.0, 40.1 (2C), 38.9, 37.2, 30.3 (d, $J_{CF}$=20 Hz), 28.2, 21.1, 20.3, 18.0, 14.3, 13.7, 13.5.

EXAMPLE 16

6-O-(1-(7-quinolyl)-3-propenyl)-11-amino-11-deoxy-3-(descladinosyl)-3-oxo-2,15-difluoroerythromycin A-11,12-cyclic carbamate 2'-O-benzoate (compound of formula (I) wherein $R^1$=F and $R^2$=benzoyl)

To a solution of 160 g of 6-O-(1-(7-quinolyl)-3-propenyl)-11-amino-11-deoxy-3-(descladinosyl)-3-oxo-15-fluoroerythromycin A-11,12-cyclic carbamate 2'-O-benzoate in 2400 mL of 1:1 dimethylformamide/tetrahydrofuran at −78° C. was added 270 mL of a 1.0 M solution of sodium bis(trimethylsilyl)amide in tetrahydrofuran. The solution was allowed to warm to −30° C. (internal temperature) over a period of 2 hours. The solution was cooled to −78° C. and 63 g of N-fluorobenzenesulfonamide was added as a solution in 400 mL of tetrahydrofuran via cannula. The solution was allowed to warm to −30° C. over 1 hour before partitioning between EtOAc (4 L) and NaHCO$_3$ (4 L). The organics were further washed with water (4 L). The combined aqueous phases were back extracted with EtOAc (1 L). The combined organics were washed with brine (2 L) and dried (MgSO$_4$) before filtering and concentrating under reduced pressure. Column chromatography (silica gel, 45% acetone-hexane, 1% $Et_3N$, followed by 60% acetone-hexane, 1% $Et_3N$) yielded the product (152 g) as a yellow solid. LC-MS: m/z=906.5 [M+H]$^+$, 453.7 [M+2H]$^{2+}$. $^{13}$C-NMR (CDCl$_3$): δ 217.7, 203.5 (d, $J_{CF}$=28 Hz), 165.1, 162.4, 156.6, 150.6, 148.6, 137.7, 135.7, 132.8 (2C), 130.2, 129.7, 128.4, 128.3, 127.9, 127.7, 124.0, 120.8, 82.6, 81.6 (d, $J_{CF}$=166 Hz), 79.3, 78.4, 75.2, 72.0, 69.3, 64.1, 63.4, 57.8, 44.1, 40.7 (2C), 40.5, 38.6, 37.2, 36.4, 31.2 (2C), 29.8 (d, $J_{CF}$=20 Hz), 24.4 (d, $J_{CF}$=22 Hz), 20.9, 17.6, 14.8, 13.7, 13.2.

EXAMPLE 17

6-O-(1-(7-quinolyl)-3-propenyl)-11-amino-11-deoxy-3-(descladinosyl)-3-oxo-2,15-difluoroerythromycin A-11,12-cyclic carbamate (Compound (III))

A solution of 149 g of 6-O-(1-(7-quinolyl)-3-propenyl)-11-amino-11-deoxy-3-(descladinosyl)-3-oxo-2,15-difluoroerythromycin A-11,12-cyclic carbamate 2'-O-benzoate in 1650 mL of methanol was heated at 50° C. for 18 hours. After cooling the solvent was concentrated under reduced pressure. The residue was triturated with 500 mL of 10% acetone/hexanes, then crystallized from 150 mL of 1:1 acetone/hexanes. The mother liquors were concentrated and chromatographed on silica gel using 50% acetone/hexanes+1% $Et_3N$ followed by 60% acetone/hexanes+1% $Et_3N$. Fractions containing product were combined and evaporated, and the residue was crystallized from 1:1 acetone/hexanes as described above. A third crop of crystals was obtained from the mother liquors as described above. Total yield of product was 64.8 g. LC-MS: m/z=802.5 [M+H]$^+$, 401.7 [M+2H]$^{2+}$. $^{13}$C-NMR (CDCl$_3$): δ 217.7, 203.9 (d, $J_{CF}$=28 Hz), 165.4 (d, $J_{CF}$=23 Hz), 156.6, 150.7, 148.7, 137.8, 135.7, 132.9, 128.5, 128.3, 128.0, 127.8, 124.1, 120.8, 104.1, 97.9 (d, $J_{CF}$=206 Hz), 82.7, 82.4, 80.8, 79.8, 79.3, 75.3, 70.4, 69.7, 65.8, 64.2, 57.9, 44.2, 40.7, 40.2 (2C), 38.9, 37.4, 30.0 (d, $J_{CF}$=20 Hz), 28.1, 24.8 (d, $J_{CF}$=21 Hz), 21.2, 21.0, 17.7, 15.4, 13.9, 13.3.

EXAMPLE 18

7-quinolyl triflate

Trifluoromethanesulfonic anhydride (28.5 mL) was added dropwise to a solution of 7-hydroxyquinoline (22.0 g) in anhydrous pyridine (100 mL) cooled on ice. After 10 minutes, the mixture was warmed to ambient temperature and stirred overnight. The mixture was poured into 1000 mL of ice-cold 1 N HCl and extracted three times with 500 mL of ether. The combined organic extracts were washed once with water and once with brine, then dried over MgSO$_4$, filtered, and evaporated. The crude product was chromatographed on silica gel (1:1 ethyl acetate/hexanes), then crystallized from hot hexane, yielding 32.3 g of product as pale yellow crystals. $^1$H-NMR (CDCl$_3$): δ 8.98 (1H, dd, J=1.6, 4.4 Hz), 8.21 (1H, d, J=7.6 Hz), 8.03 (1H, d, J=2.4 Hz), 7.91 (1H, d, J=8.8 Hz), 7.48 (2H, m). $^{13}$C-NMR (CDCl$_3$): δ 151.4, 149.9, 146.9, 137.3, 130.4, 127.5, 122.3, 121.1, 120.2, 118.7 (q, $J_{CF}$=320 Hz).

EXAMPLE 19

6-O-(1-(7-quinolyl)-3-propenyl)-11-amino-11-deoxy-3-(descladinosyl)-3-oxo-2,15-difluoroerythromycin A-11,12-cyclic carbamate 2'-O-propionate (Compound of Formula (I) Wherein $R^1$=F and $R^2$=CH$_3$CH$_2$CO)

A solution of 6-O-(1-(7-quinolyl)-3-propenyl)-11-amino-11-deoxy-3-(descladinosyl)-3-oxo-2,15-difluoroerythromycin A-11,12-cyclic carbamate (800 mg) and propionic anhydride (260 mg) in 5 mL of ethyl acetate is stirred for 16 hours at ambient temperature. The mixture is washed with sat. aq. NaHCO$_3$, then dried over MgSO$_4$, filtered, and evaporated. The residue is chromatographed on silica gel using a gradient from 10% to 80% acetone in hexanes containing 1% $Et_3N$.

EXAMPLE 20

6-O-(1-(7-quinolyl)-3-propenyl)-11-amino-11-deoxy-3-(descladinosyl)-3-oxo-15-fluoroerythromycin A-11,12-cyclic carbamate 2'-O-propionate (compound of formula (I) wherein $R^1$=H and $R^2$=CH$_3$CH$_2$CO)

A solution of 6-O-(1-(7-quinolyl)-3-propenyl)-11-amino-11-deoxy-3-(descladinosyl)-3-oxo-15-fluoroerythromycin A-11,12-cyclic carbamate (780 mg) and propionic anhydride (260 mg) in 5 mL of ethyl acetate is stirred for 16 hours at ambient temperature. The mixture is washed with sat. aq. NaHCO$_3$, then dried over MgSO$_4$, filtered, and evaporated. The residue is chromatographed on silica gel using a gradient from 10% to 80% acetone in hexanes containing 1% $Et_3N$.

EXAMPLE 21

Microbiological Activity

Minimum inhibitory concentrations ("MICs") were determined by the NCCLS broth microdilution procedure for susceptibility testing for bacteria that grow aerobically (National Committee for Clinical Laboratory Standards, 1997. Methods for dilution antimicrobial susceptibility tests for bacteria that grow aerobically, 4$^{th}$ ed. Approved standard. NCCLS Document M7-A4. National Committee for Clinical Laboratory Standards, Villanova, Pa.). Stock solutions were prepared on the day of the test and appropriate aliquots were added to cation adjusted Mueller-Hinton broth (CAMHB, DIFCO) or *Haemophilus* test media. Two-fold serial dilutions were prepared and added to wells in microtiter plates. Final test concentrations ranged from 8 to 0.004 ug/ml. Broth cultures of bacteria inoculated from growth on overnight plates for all test bacteria except *Streptococcus pneumoniae* and *Haemophilus influenzae* were incubated at 35° C. and then adjusted to the Kirby Bauer standard and diluted in CAMHB to achieve a final inoculum concentration of approximately 5×10$^5$ CFU/ml. Inocula for *S. pneumoniae* and *H. influenzae* were prepared by directly suspending colonies from an overnight plate, adjusting the turbidity and diluting as above. *S. pneumoniae* media was supplemented with 3% lysed horse blood. All plates were incubated in ambient air at 35° C. for 20-24 h for *S. pneumoniae* and *Haemophilus influenzae* and 16-20 h for all other bacteria. The MIC endpoints were determined by reading the lowest concentration of test compound that completely inhibited the growth of the test bacteria. Results for compounds described in the above Examples are listed in Table 11.

TABLE 11

MIC values (μg/mL) against respiratory pathogens.

| Species | Genotype | clarithromycin | | Compound (II) | | Compound (III) | |
|---|---|---|---|---|---|---|---|
| | | MIC$_{50}$ | MIC$_{90}$ | MIC$_{50}$ | MIC$_{90}$ | MIC$_{50}$ | MIC$_{90}$ |
| S. pneumoniae | sensitive | 0.06 | 0.06 | 0.03 | 0.03 | 0.03 | 0.03 |
| | ermB | >8 | >8 | 0.12 | 0.12 | 0.12 | 0.12 |
| | mef | 4 | 8 | 0.25 | 0.25 | 0.25 | 0.25 |
| | ermB + mef | >8 | >8 | 1 | 2 | 0.5 | 1 |
| S. pyogenes | sensitive | 0.06 | 0.06 | 0.03 | 0.03 | 0.06 | 0.06 |
| | ermB | >8 | >8 | 0.12 | 1 | 0.12 | 1 |
| | mef | 8 | >8 | 0.12 | 0.25 | 0.12 | 0.12 |
| H. influenzae | sensitive | 8 | 8 | 2 | 4 | 2 | 4 |
| | resistant | >8 | >8 | >8 | >8 | >8 | >8 |
| M. catarrhalis | | 0.12 | 0.12 | 0.12 | 0.12 | 0.12 | 0.12 |

MIC$_{50}$ = minimum concentration needed to inhibit growth of 50% of the strains.
MIC$_{90}$ = minimum concentration needed to inhibit growth of 90% of the strains.

EXAMPLE 22

In Vivo Efficacy

The in vivo efficacy of compounds (II) and (III) were evaluated in a rat lower respiratory tract infection model. Groups of 8 rats were infected intratracheally with 0.5 mL containing 10$^6$ CFUs of *Streptococcus pneumoniae* ATCC 6303 in 5% hog gastric mucin. Compounds dissolved in ethanol were administered by oral gavage daily over 3 days starting 18 hours post-inoculation. Lungs were aseptically removed from survivors 12 hours after the last dose and examined for visible signs of infection, then homogenized in sterile PBS and plated for determination of CFUs by log plating on Columbia agar-nalidixic acid plates. As shown in Table 12, both compounds (II) and (III) were efficacious at reducing the bacterial load in the rat lungs and increasing survival relative to control animals.

TABLE 12

In vivo efficacy of compounds (II) and (III) in the rat lung pneumonia model.

| | Log CFU/g (avg, n = 8) | Range | % survivors |
|---|---|---|---|
| Control | 6.5 | 2.7-8.6 | 62% |
| (II) 0.5 mg/kg | 4.8 | 2.7-8 | 78% |
| (II) 2.5 mg/kg | 4.3 | 3.1-8 | 88% |
| (III) 0.5 mg/kg | 3.9 | 2.8-5.9 | 100% |
| (III) 2.5 mg/kg | 3.0 | 2.7-3.3 | 100% |

EXAMPLE 23

Antibacterial Testing Against Propionibacteria

Minimum inhibitory concentrations ("MICs") were determined by the NCCLS Reference Agar Dilution Method (M11-A5, Vol. 21, No. 2) for anaerobic bacteria. A panel of 84 antibiotic-susceptible and resistant strains of Propionibacteria from distinct geographic locations were selected. Following revival from frozen stocks, each strain was purity plated onto Wilkins Chalgren Agar, pH 7.2 (Oxoid, UK), and the appropriate antibiotic resistance/susceptibility phenotype was confirmed by antibiotic disc testing. Each strain was subjected to an agar dilution MIC assay. Stock solutions of compound (III) in DMSO were added to ranges of agar plates in doubling concentrations from 0.0625 to 128 μg/mL. As comparators, erythromycin (in ethanol) was tested from 0.0625 to 128 μg/mL and clindamycin (in water) was tested from 0.0625 to 512 μg/mL. The inocula for each batch of strains were prepared from 7-day old Wilkins Chalgren Agar plate cultures by resuspension of colonies in Wilkins Chalgren Anaerobe broth, pH 7.2 (Oxoid, UK) to an optical density (OD$_{600}$) of 0.2±0.02. The inoculum (1.0-2.0 μL) for each strain was applied to a Wilkins Chalgren Agar MIC plate in a grid pattern using a Multipoint Inoculator (Denley, UK). All agar plates were incubated at 37° C. for 3 days under anaerobic conditions in AnaeroPack 7 liter rectangular jars (Mitsubishi Gas Chemical Company, Inc., Japan). Anaerobic conditions were achieved in each jar by the addition of two GENbox anaer sachets (Biomerieux, France). MIC values determined by this method are given in Table 13.

TABLE 13

Minimum Inhibitory Concentrations (MIC) in μg/mL against sensitive and resistant *Propionibacteria*.

| Species | Resistance marker | phenotype | MIC range erythromycin | clindamycin | (III) |
|---|---|---|---|---|---|
| P. acnes | ermX | EryR | >128 | >512 | 32-128 |
| P. granulosum | ermX | EryR | >128 | 512 | 4-32 |
| P. acnes | RNA 2057 | EryR | 4 | 1 | 0.06 |
| P. acnes | RNA 2058 | EryR | >128 | 8-256 | 0.125-2 |
| P. granulosum | RNA 2058 | EryR | >128 | 512 | 8 |
| P. acnes | RNA 2059 | EryR | >128 | 8-256 | 0.125-2 |
| P. granulosum | RNA 2059 | EryR | >128 | 2-512 | 0.125-2 |
| P. acnes | RNA 2058 | EryR, TetR | >128 | 2-256 | 0.06-1 |
| P. acnes | RNA 1058/2058 | TetR, EryR | >128 | 256 | 1-2 |
| P. acnes | RNA 1058/2059 | TetR, EryR | >128 | 8-16 | 0.5 |
| P. acnes | RNA 2059 | EryR, TetR | >128 | 8-32 | 0.06->128 |
| P. acnes | RNA 1058 | TetR | 0.06->128 | 0.25-256 | 0.06-1 |
| P. acnes | unknown | ClindR | 0.06-0.125 | 4 | 0.06 |
| P. acnes | none | none | 0.06 | 0.125-1 | 0.06 |
| P. granulosum | none | none | 0.06-8 | 0.06-0.25 | 0.06 |

Strains with resistance markers indicated as "ermX" contain the ribosomal methylase; those marked as "RNA" have mutations at the indicated base in either the 23S RNA (RNA 2057, 2058, 2059) or 16S RNA (RNA 1058) sequences.

EXAMPLE 24

Cardiovascular Safety of Compounds of Formulas (VIII) and (II) in Rats and Guinea Pigs Total doses of drug (0.47, 0.94, 1.88, 3.75, 7.5, and 15 mg/kg) or equivalent volumes of vehicle were administered incrementally as an i.v. bolus to groups of 6 anesthetized rats or guinea pigs at 0, 15, 30, 45, 60, and 75 minutes. Hemodynamic parameters including mean arterial pressure (MAP) and heart rate (HR), and ECG parameters (QT and PR intervals and QRS duration) were recorded. For the rat, injection of vehicle gave a 16% increase in QT interval over baseline. For the guinea pig, injection of vehicle gave a 3% increase in QT interval over baseline. The data are summarized in Tables 14 and 15.

TABLE 14

Effect of compounds of formula (VIII) and (II) on QT interval in the rat.

| Compound | Z | $R^8$ | QT prolongation (% above vehicle) |
|---|---|---|---|
| A | 3-quinolyl | H | 8 |
| B | 3-quinolyl | F | 10 |
| C | 6-quinolyl | H | 20 |
| D | 1,5-naphthyrid-3-yl | H | 28 |
| E | 6-chloro-3-quinolyl | H | (toxic) |
| G | 6-quinoxalyl | H | 12 |
| H | 6-quinoxalyl | F | 15 |
| (II) | | | −4 |

TABLE 15

Effect of compounds of formula (VIII) and (II) on QT interval in the guinea pig.

| Compound | Z | $R^8$ | $QT_c$ prolongation (% above vehicle) |
|---|---|---|---|
| A | 3-quinolyl | H | 10 |
| B | 3-quinolyl | F | 3 |
| C | 6-quinolyl | H | 12 |

TABLE 15-continued

Effect of compounds of formula (VIII) and (II) on QT interval in the guinea pig.

| Compound | Z | $R^8$ | $QT_c$ prolongation (% above vehicle) |
|---|---|---|---|
| D | 1,5-naphthyrid-3-yl | H | 14 |
| G | 6-quinoxalyl | H | 1 |
| H | 6-quinoxalyl | F | 4 |
| (II) | | | 1 |

EXAMPLE 25

Detailed Cardiovascular Safety of Compounds (II) and (III) in Dogs

Four male beagle dogs, obtained from Marshall Farms USA, Inc. (North Rose, N.Y.), were surgically instrumented with telemetry transducers (Data Sciences International, type RL11M2-D70-PCT) to assess arterial blood pressure (ABP) and lead II electrocardiogram (ECG) parameters.

The dosing route was an intravenous infusion jugular vein access). The infusion was accomplished using a CADD Prizm® ambulatory infusion pump attached to a jacket worn by the dog. The dose duration for the intravenous infusion was 30 min for all doses administered, except the last dose (30 mg/kg) where the infusion period was extended to 45 min to accommodate the larger dose volume required for this dose. The vehicle dose and diluent for the test article was 0.05-M sodium citrate in sterile water for injection.

There was one treatment group of four non-naïve dogs and the study was comprised of both pharmacokinetic and telemetry phases, as summarized in the dose administration table for compound (III) (Table 16) below. At least one week was given between dosings to allow clearance of the drug.

TABLE 16

Summary of dose administration in cardiovascular safety testing

| Dose Day | n | Route of Administration | Study Phase | Nominal Concentration (mg/mL) | Dose Volume (mL/kg) | Nominal Dose (mg/kg) |
|---|---|---|---|---|---|---|
| 1 | 4 | Intravenous | Telemetry | 2.67 | 3 | 8 |
| 2 | 4 | Intravenous | PK | 3.67 | 3 | 11 |
| 3 | 4 | Intravenous | Telemetry | 3.24 | 3.4 | 11 |
| 4 | 4 | Intravenous | Telemetry | 3.158 | 5 | 15 |
| 5 | 4 | Intravenous | PK | 3.158 | 5 | 15 |
| 6 | 2 | Intravenous | PK | 3.1 | 8.5 | 25 |
| 7 | 4 | Intravenous | Telemetry | 3.1 | 10.2 | 30 |

For the pharmacokinetic (PK) phase, the blood collection intervals were: predose, 10, 20, 30, (end dose time), 35, 45, 60, 90, 150, 270, 390, 510, 1440, and 2880 min relative to the start of the infusion. Whole blood (~2 mL) was collected into Vacutainerss' (BD, Franklin, N.J.) containing sodium heparin as the anticoagulant agent. Blood samples were centrifuged at a speed of 3000 rpm, a temperature of 4° C. and a run time of 10 min. Plasma samples were transferred to amber glass vials and analyzed by LC/MS/MS to determine drug concentrations.

For the telemetry phase of the study, collection of hemodynamic and lead II ECG data commenced approximately 30 min prior to dosing and ended approximately 6 h post-dose. Systolic blood pressure (SBP), diastolic blood pressure (DBP), HR, and lead II ECG variables (PR interval, QRS duration, RR interval, and QT interval) were acquired continuously from each animal during each dose day recording session. The QT interval was corrected for variations in HR using the Fridericia's QTc interval (QTcF).

Data acquired following treatment with vehicle or compound (III) were extracted at −10, −5, 0, 10, 20, 30, 35, 45, 60, 90, 150, 270, and 390 min relative to the start dose time. For all blood pressure and ECG parameters, data following treatment with compound (III) were compared to the time-matched vehicle dose data. Statistical comparisons were made using a one-way ANOVA for repeated measures, followed by the Dunnett's post-hoc test when statistical significance was detected with the ANOVA. Changes were considered statistically significant when $p<0.05$.

A complete visual scan of the ECG waveforms from the vehicle, 11 mg/kg dose, and 15 mg/kg dose of compound (III) was conducted. All waveforms were examined for gross changes in waveform morphology and arrhythmogenesis.

The mean concentration-time data for the 11 mg/kg dose of compound (III) demonstrated that exposure to the test article increased rapidly during the 30 min intravenous infusion period in all four male beagle dogs studied. Mean $C_{max}$ for compound (III) was 6004±1132 ng/mL with $AUC_{tot}=$ 33907±3190 ng/mL-h. The mean $T_{max}$ value was 0.46±0.08 h, which is consistent with the route and method of administration for the study. Compound (III) plasma levels gradually declined after reaching $C_{max}$ and the mean half-life was 5.36±0.40 h. For the two 15 mg/kg doses, mean $C_{max}$ was 7515±3307 and 6206±3144 ng/mL, and the $AUC_{tot}$ was 43895±23125 and 36047±22104 ng/mL·h, respectively, for the four dogs studied.

ABP parameters (systolic pressure (SBP), diastolic pressure (DBP), and mean arterial pressure (MAP)) remained relatively unchanged during and up to 150 min after intravenous infusion of the vehicle and compound (III) at doses of 11, 15, and 30 mg/kg. There was a tendency for SBP, DBP, and MAP to be increased after treatment at the 11 and 15 mg/kg doses, when compared to the vehicle control, at the 270- and 390-min time points. The increase in ABP parameters was not dose-related. Only the increase in SBP for the 11 mg/kg dose group at 390 min postdose was significantly ($p<0.05$) different from the vehicle control.

Compound (III), at a dose of 11 mg/kg, had no effect on mean HR, when compared to the time-matched vehicle control dose. Significant ($p<0.05$) decreases in mean HR were detected for the 15 mg/kg dose group, relative to the vehicle control, at the 90 and 390 time points. There was also a statistically significant ($p<0.05$) reduction in the HR at 390 min postdose after treatment with the high dose (30 mg/kg) of compound (III).

The changes in blood pressure and HR, relative to the vehicle control, do not appear to be test article related, since the effect is not dose-dependent, the time is not consistent with a $T_{max}$ of ~0.5 hr, and the blood pressure and HR values from 90 to 390 min are similar to corresponding pre-dose baseline values for each respective dose level studied. The changes in blood pressure and HR observed most likely reflect daily variation from one study day to another.

Figure 6:
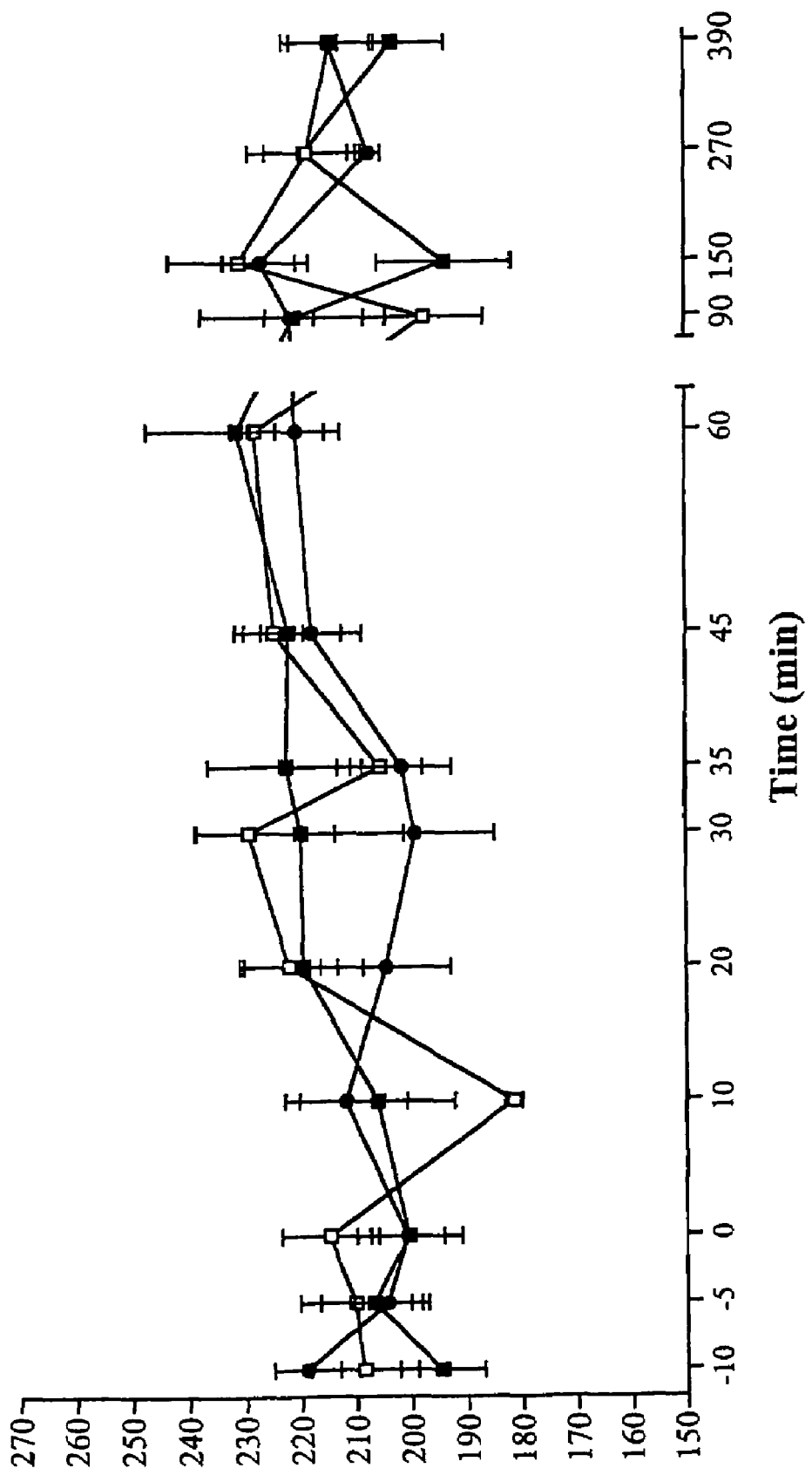
FIG. 6 shows the effects of intravenous infusion of vehicle (open squares) or of the compound of the invention having formula (III) at either 11 mg/kg (solid squares) or 15.8 mg/kg (solid circles) on the heart rate-corrected QT interval (QTc in msec) in male beagle dogs. Infusion began at 0 minutes and continued over 30 minutes. No significant increase in QTc was observed.

The effects of intravenous administration of vehicle and compound (III), at dose levels of 11 and 15 mg/kg, on QTc in male beagle dogs are shown in FIG. 6.

No significant effects on the PR interval were detected during or after intravenous compound (III) administration at doses of 11 and 15 mg/kg, when compared to the vehicle dose. Administration of the high dose level (30 mg/kg) of compound (III) resulted in an increase in the PR interval, relative to the vehicle control from 150 to 390 min. The increase in PR interval was statistically significant ($p<0.05$) at the 390-min time point. There was no effect on the QRS duration after treatment with the 11 mg/kg dose of compound (III). Significant ($p<0.05$) decreases in QRS duration, relative to the vehicle control, were detected after intravenous infusion of compound (III) at doses of 15 and 30 mg/kg. However, QRS duration was also lower at both of the pre-drug baseline values (at −10 and −5 min) on these dose days, when compared to the baseline values observed on the vehicle dose day. The reason for the consistently lower QRS duration on the 15 and 30 mg/kg dose days is not readily apparent, since a consistent effect on HR was not observed for the dogs on this dose day. The QRS duration values for these dose groups are still well within the range considered to be normal for beagle dogs.

The RR interval remained relatively unchanged during the study period in the vehicle and compound (III) treatment groups. A significant ($p<0.05$) decrease in the 11 mg/kg dose group at 150 min, a significant ($p<0.05$) increase in the 15 mg/kg dose group at 390 min, and a significant ($p<0.05$) increase in the 30 mg/kg dose group at 390 min were detected; however, these changes were thought to be spurious, given the transient nature of the changes and the lack of dose or time dependency.

There were no significant effects on the QT interval, relative to the vehicle control, during or after intravenous administration of compound (III) at doses of 11, 15, or 30 mg/kg. The QT interval was corrected for variations in the HR using the QTcF correction method. Compound (III), at doses of 11 and 15 mg/kg, had no significant effects on QTcF over the course of the study. There was a lengthening of the QTcF interval from 35 to 90 min postdose after treatment with 30 mg/kg compound (III), when compared to the time-matched vehicle control. There were no abnormalities in waveform morphology or ECG rhythm during or after administration of compound (III) at doses of 11 or 15 mg/kg.

Figure 5:
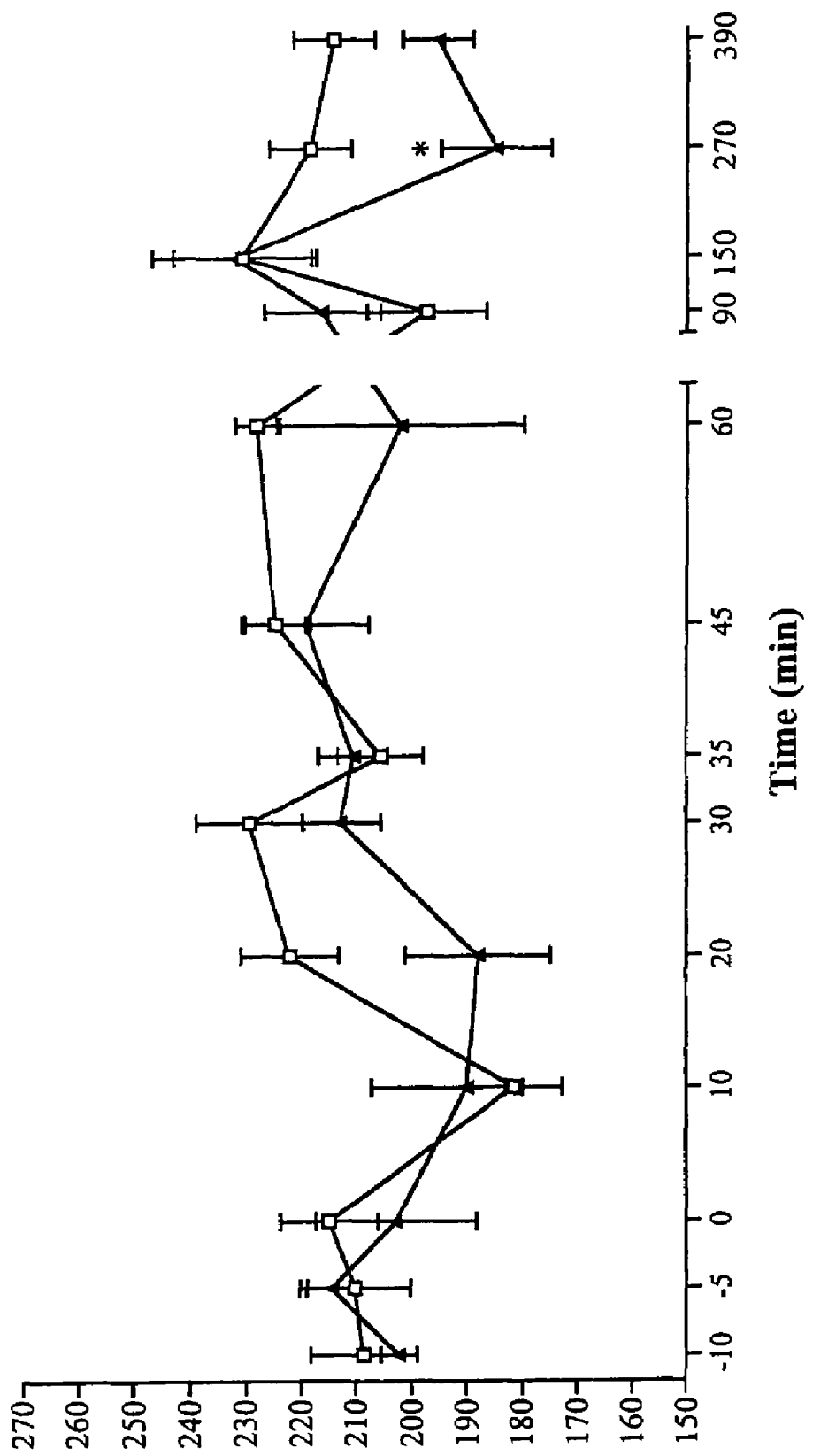
FIG. 5 shows the effects of intravenous infusion of vehicle (open squares) or 15 mg/kg of the compound of the invention having formula (II) (solid triangles) on the heart rate-corrected QT interval (QTc in msec) in male beagle dogs. Infusion began at 0 minutes and continued over 30 minutes. No significant increase in QTc was observed.

Similar experiments were performed with compound (II). The effect of intravenous administration of vehicle and compound (II) at a dose level of 15 mg/kg, on QTc in male beagle dogs is shown in FIG. 5.

EXAMPLE 26

In Vitro Hepatotoxicity

In one experiment, hepatotoxicity was estimated by overnight incubation of compounds at 3, 10, 30, 100, or 300 µM with cultured rat or human hepG2 hepatocytes, followed by staining of the cells with resazurin to measure viability or with Nile Red to measure steatosis. The minimal drug concentration at which changes in dye binding were observed was noted as the minimal effective concentration. The compound of formula (VIII) wherein Z=3-quinolyl affected metabolic stability and steatosis in human HepG2 hepatocytes at 30 µM. No effects were observed with the compound of formula (VIII) wherein Z=6-quinoxalyl or compound (III) at 100 µM.

In a second experiment, the hepatotoxicity of compound (III) was estimated using cryopreserved human hepatocytes pooled from four donors, measuring leakage of cellular lactate dehydrogenase (LDH). Each donor was selected for the study based on the activity of cytochrome P450 (phase I) and uridine diphosphoglucuronosyl transferases (phase II). Hepatocytes were initially prepared from human livers by collagenase perfusion and subsequently cryogenically frozen. Viable cryopreserved hepatocytes were enriched in accordance with BD Biosciences Discovery Labware SOP HP-10. Hepatocytes were rapidly thawed, pooled and incubated in Williams' E medium at a density of $2 \times 10^6$ cells/ml at 37° C. in an incubator for 30 min. After incubation, the viable cells were separated with 24% Percoll gradient and resuspended in WME at a density of $1 \times 10^6$ cells/ml. Initial viability was determined by trypan blue exclusion. Hepatocytes were incubated in a 24-well plate and each well contained $0.25 \times 10^6$ cells in 0.5 ml of WME medium. Three wells were used for determination of total LDH activity (cells+media) and the background activity (incubation media only) at the 0 time point. Briefly, a 100 µl aliquot of cell suspensions from these wells was immediately taken and rapidly centrifuged at 14,000 rpm for 15 seconds. The supernatants were transferred to microcentrifuge tubes and stored at ≦4° C. for measurement of LDH activity present in medium at the 0 time point. Another 100 µl aliquot of cell suspension from same wells was removed, mixed with 100 µl of 0.4% Triton and stored at ≦4° C. for measurement of total LDH activity.

Hepatocytes in other wells were incubated with test article at the concentrations of 200, 67, 22, 7.4, 2.5 and 0.82 µM. Six concentrations of test article, a single concentration of positive control tamoxifen, and solvent vehicle controls were tested in triplicate. Hepatocytes were exposed to the test substance and the positive control for 4 hours. After incubation, 100 µl aliquots of cell suspensions were taken and rapidly centrifuged at 14,000 rpm for 15 seconds. The supernatants were transferred to microcentrifuge tubes and stored at ≦4° C. for measurement of LDH activity in incubation medium. The positive control used for hepatocyte toxicity was 100 µM tamoxifen. The solvent for tamoxifen delivery was DMSO (final concentration: 0.1%).

LDH activity in both total (medium+cells) and medium was determined by monitoring the enzymatic formation of NADH from $NAD^+$ in the presence of L-lactic acid [1]. Briefly, post-centrifugation supernatants were diluted 1:40 with phosphate-buffered saline (pH 7.4). A 100 µl aliquot was mixed with 100 µl LDH reagent containing 7.5 mM $NAD^+$, 50 mM L-lactic acid in 250 mM Tris-HCl buffer (pH 8.9) in a 96-well plate. The increase in fluorescence due to the formation of NADH were kinetically monitored at Ext. 360 nm, Em. 460 nm, using a Fluorescence plate reader. The percent LDH leakage from cells was calculated by comparing incubation medium values with total LDH activity (see Equation below). The cell viability at each concentration of test articles was reported.

% LDH leakage=(LDH activity in medium sample/ total LDH activity)*100

The data are summarized in Table 17. The LDH leakage from the hepatocytes was slightly increased by approximately 5% in vehicle control group after 240 min of incubation. Treatment of hepatocyte suspensions with positive control tamoxifen at 100 µM caused 63% increase in LDH leakage. Incubation of the hepatocytes with compound (III) at 0.82, 2.5. 7.4, 22, 67, and 200 µM for 240 min did not increase LDH leakage, as compared with that in solvent (DMSO) vehicle-treated cells.

TABLE 17

Results of in vitro hepatotoxicity tests on compound (III).

| Concentration | Compound (III) | |
| --- | --- | --- |
| (µM) | *LDH leakage (%) | Viability (%) |
| 0.5 mM Citrate buffer | 5.5 ± 0.75 | 94 ± 0.75 |
| 0.82 | 6.1 ± 0.63 | 94 ± 0.63 |
| 2.5 | 3.9 ± 2.8 | 96 ± 2.8 |
| 7.4 | 10 ± 2.9 | 90 ± 2.9 |
| 22 | 12 ± 0.74 | 88 ± 0.74 |
| 67 | 6.7 ± 1.3 | 93 ± 1.3 |
| 200 | 7.6 ± 4.2 | 92 ± 4.2 |
| Positive control | | |
| DMSO | 12 ± 4.0 | 88 ± 4.0 |
| Tamoxifen (100 µM) | 63 ± 1.0 | 37 ± 1.0 |

EXAMPLE 27

Pharmacokinetics

The pharmacokinetics of compounds of formula (VIII) and compounds of formula (II) and (III) were measured in the mouse. Compounds were administered either intravenously (i.v.) at 1 mg/kg, or per oral gavage (p.o.) at 10 mg/kg. Plasma samples were taken and analyzed by LC/MS-MS. For lung tissue pharmacokinetics, lungs were removed and homogenized, followed by analyzis by LC/MS-MS. Results for p.o. administration are given in Table 18.

TABLE 18

Comparison of pharmacokinetic parameters for 15-fluoroketolides of formulas (VIII), (II), and (III) in the mouse. Mice were dosed per oral gavage with 10 mg/kg of compound.

|  | (VIII) | (VIII) | (VIII) | (VIII) | (II) | (III) |
|---|---|---|---|---|---|---|
| Plasma formula |  |  |  |  |  |  |
| Z = | 3-quinolyl | 3-quinolyl | 6-quinoxalyl | 6-quinoxalyl |  |  |
| $R^8$ | H | F | H | F |  |  |
| Cmax (ug/mL) | 0.4 | 1.0 | 0.21 | 0.67 | 0.26 | 3.0 |
| AUC (ug/mL-h) | 0.7 | 3.9 | 0.54 | 2.1 | 0.89 | 16.e2 |
| Lung formula |  |  |  |  |  |  |
| Z | 3-quinolyl | 3-quinolyl | 6-quinoxalyl | 6-quinoxalyl |  |  |
| $R^8$ | H | F | H | F |  |  |
| Cmax (ug/mL) | 0.8 | 3.3 | 0.45 | 3.0 | 0.26 | 8.7 |
| AUC (ug/mL-h) | 2.3 | 19.0 | 2.2 | 11.0 | 1.42 | 45.9 |

EXAMPLE 28

Skin Penetration Studies of Topical Formulations

The penetration of compound (III) formulated in various vehicles into human skin was determined. Franz static diffusion cells (15 mm diameter orifice, o-ring joint) were mounted on 9-cell manifolds and maintained at a constant temperature by use of re-circulating water baths set at 32° C. These cells have an opening with a nominal area of 1.77 cm$^2$ and a receptor compartment with a volume ranging between 12 to 14 ml. Each diffusion cell was assembled by placing a disk shaped section of excised human skin (obtained from elective surgery) over the orifice of the receptor (bottom) compartment. A Teflon® O-ring was placed on top of the skin before the donor cap was added (top compartment). This diffusion area was then secured in place by a pinch clamp, ensuring an adequate seal between the donor and receptor compartments. The joint between the donor and receptor compartments of each cell was wrapped with Parafilm® (American Can Company) to prevent evaporation of the receptor phase. Each cell was then filled with the receptor phase consisting of phosphate buffered saline with 0.1% sodium azide and 4% bovine serum albumin (w/w/w) at 32° C. Any air bubbles present under the tissue were removed prior to dosing. The receptor phase was continuously stirred using a Teflon magnetic stir bar and an inoculating loop cut to 6.0 cm from the top of the loop. The systems were equilibrated with the receptor phase for 1 hour prior to formulation application.

Approximately 10 mg/cm$^2$ of each formulation was dosed onto the tissue surfaces of five cells. Each formulation was applied in an alternating fashion to diffusion cells in at least two separate Static Cell Systems. The sampling ports were sealed with Parafilm to prevent evaporation. Collection of nominally 1 mL receptor phase sample was preformed at four hours. The samples were removed through the sampling port using a syringe fitted with Teflon tubing on the needle and transferred into plastic scintillation vials. After the first collection (4 hours), the receptor compartment was refilled with fresh receptor phase maintained at 32° C. The whole content of each cell was collected and weighed at 24 hours after dosing. Tissue samples at the end of the experiment were dissected into epidermis and dermis, and extracted with acetonitrile prior to analysis. Samples were analyzed for drug content by LC/MS-MS.

In a first experiment, compound (III) was dissolved at 0.5% (w/v) in ethanol (EtOH), methylsulfoxide (DMSO), propylene glycol (PG), or dibutyl sebacate (DBS), or at 2.0% in dibutyl sebacate. The data are summarized in Table 19.

TABLE 19

Distribution of Compound (III) into receptor fluid (4 and 24 hrs), epidermis, and dermis. Columns show average amount (n = 5) of compound (ng) found in indicated compartment

| Formulation | Receptor (4 h) | Receptor (24 h) | Epidermis | Dermis | Total |
|---|---|---|---|---|---|
| 0.5% EtOH | 2 | 28 | 2740 | 1580 | 4350 |
| 0.5% PG | 0.5 | 7 | 3210 | 2240 | 5458 |
| 0.5% DMSO | 52 | 669 | 9240 | 1520 | 11481 |
| 0.5% DBS | 1 | 27 | 363 | 4140 | 4532 |
| 2% DBS | 3 | 172 | 2170 | 11860 | 14205 |

The cumulative skin penetration of compound (III) into receptor fluid after 24 hours of exposure ranged from 0.005 to 0.82% of the applied dose. Dibutyl sebacate exhibited statistically significantly greater percent penetration than either ethanol or propylene glycol. Epidermal deposition ranged from 0.42 to 11% of the applied dose. Highest dermal penetration (5.7% of applied dose) was observed with dibutyl sebacate.

In a second experiment, more complex ethanolic gel formulations were studied (Table 20). Each formulation comprised hydroxypropylcellulose (HPC) at 2% (w/w) as a gelling agent.

TABLE 20

Composition (% w/w) of ethanolic gel formulations

| formulation component | % (w/w) | | | | |
|---|---|---|---|---|---|
| | 18A | 18B | 18C | 19A | 19B |
| Compound (III) | 1.0 | 1.0 | 1.0 | 1.0 | 1.0 |
| DBS | 0 | 10.0 | 20.0 | 0 | 0 |
| Transcutol | 0 | 0 | 0 | 10.0 | 10.0 |
| Benzyl alcohol | 0 | 0 | 0 | 0 | 2.0 |
| Propylene glycol | 10.0 | 0 | 0 | 10.0 | 10.0 |
| HPC | 2.0 | 2.0 | 2.0 | 2.0 | 2.0 |
| Ethanol | 87.0 | 87.0 | 77.0 | 77.0 | 75.0 |

Cumulative skin penetration of compound (III) after 24 hours of exposure ranged from 0.0088 to 2.18 percent of the dose applied from formulations 19B and 18C, respectively.

Tissue levels of compound (III) following the 24-hour exposure were measured. Epidermal deposition ranged from 2.12 to 7.93 percent of the dose applied from formulations 18A and 18B, respectively. Formulation 18C has the next highest epidermal level with 6.41 percent of the dose applied. Dermal deposition ranged from 0.0676 to 1.62 percent of the dose applied from formulations 18A and 18C, respectively. Formulation 18B has the next highest dermal level with 1.45 percent of the dose applied.

Formulations 18B and 18C, comprising dibutyl sebacate, demonstrated the highest levels of skin deposition and penetration for compound (III).

EXAMPLE 29

Construction of *Streptomyces coelicolor* K460-2

To create a plasmid for the expression of the truncated 6-deoxyerythronolide B synthase ("DEBS") under the actinorhodin promoter, actIp, in a SCP2 vector, the DEBS expression plasmid pKOS146-103A, described in Desai et al., "Combining classical, genetic, and process strategies for improved precursor-directed production of 6-deoxyerythronolide B analogues," *Biotechnol. Prog.* 20: 38-43 (2004), incorporated herein by reference, was cut with SpeI and HindIII to obtain a circa 34.1 kbp fragment and with HindIII and NdeI to generate a circa 3.7 kbp fragment. The plasmid pKOS214-119 described in Regentin et al., "Precursor-directed biosynthesis of novel triketide lactones," *Biotechnol. Prog.* 20: 122-127 (2004), incorporated herein by reference, which contains DEBS module 2 with an N-terminal DEBS module 5 linker, was digested with NdeI and SpeI generating a circa 4.3 kbp fragment. These three fragments were ligated to give the expression plasmid pKOS279-7A. The plasmid pKOS146-145 was described in Hu et al., "Enhanced heterologous polyketide production in *Streptomyces* by exploiting plasmid co-integration," *J. Ind. Microbiol. Biotechnol.,* 30:512-522 (2003), incorporated herein by reference.

Plasmids pKOS146-145 and pKOS279-7A were introduced into *Streptomyces coelicolor* K146-151B, described in Desai et al., "Combining classical, genetic, and process strategies for improved precursor-directed production of 6-deoxyerythronolide B analogues," *Biotechnol. Prog.* 20: 38-43 (2004), incorporated herein by reference, using protoplast transformation as described in Kieser et al., *Practical Streptomyces Genetics*, Crowes, Norwich, England (2000), incorporated herein by reference, employing selection for apramycin and thiostrepton resistance to produce *Streptomyces coelicolor* K460-2.

All references cited herein are hereby incorporated by reference if not otherwise specifically indicated.

What is claimed is:

1. A compound or pharmaceutically acceptable salt thereof having the formula

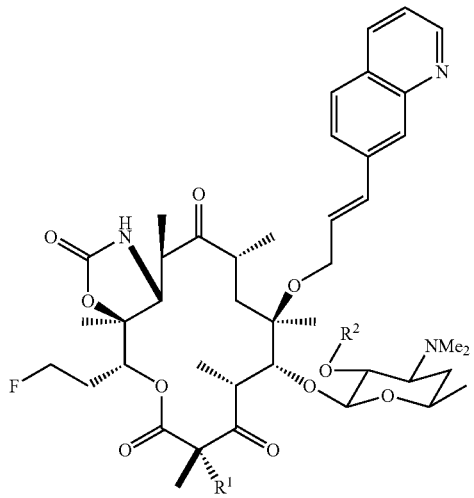

wherein $R^1$ is H or F and $R^2$ is H or a hydroxyl protecting group.

2. A compound or pharmaceutically acceptable salt thereof of claim 1 wherein $R^1$ is H or F and $R^2$ is H or $R^3CO$, wherein $R^3$ is substituted or unsubstituted $C_1$-$C_5$ alkyl or substituted or unsubstituted aryl.

3. The compound or pharmaceutically acceptable salt thereof of claim 1 wherein $R^1$ is H.

4. The compound or pharmaceutically acceptable salt thereof of claim 1 wherein $R^1$ is H and $R^2$ is H or $R^3CO$, wherein $R^3$ is $CH_3$, $CH_3CH_2$, $CH_3CH_2O(C=O)CH_2CH_2$, or phenyl.

5. The compound or pharmaceutically acceptable salt thereof of claim 1 wherein $R^1$ is H and $R^2$ is H.

6. The compound or pharmaceutically acceptable salt thereof of claim 1 wherein $R^1$ is F.

7. The compound or pharmaceutically acceptable salt thereof of claim 1 wherein $R^1$ is F and $R^2$ is H or $R^3CO$, wherein $R^3$ is $CH_3$, $CH_3CH_2$, $C_3C_2O(C=O)CH_2CH_2$, or phenyl.

8. The compound or pharmaceutically acceptable salt thereof of claim 1 wherein $R^1$ is F and $R^2$ is H.

9. A pharmaceutical composition comprising a compound of claim 1 or pharmaceutically acceptable salt thereof together with a pharmaceutically acceptable carrier.

10. A pharmaceutical composition of claim 9, wherein the pharmaceutical composition comprises a compound or pharmaceutically acceptable salt thereof having the formula

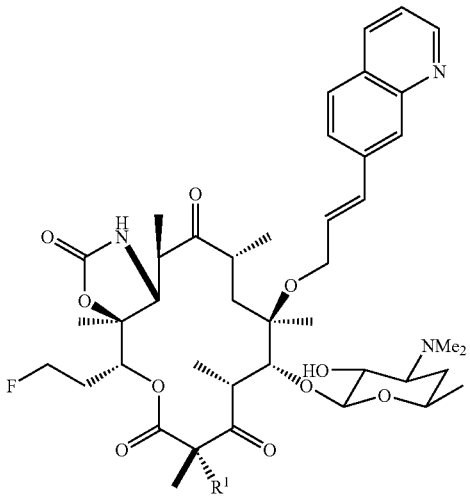

wherein $R^1$ =H or F.

11. A pharmaceutical composition of claim 10 suitable for topical application, wherein the pharmaceutical composition is a solution, gel, crème, suspension, lotion, foam, or ointment.

12. A pharmaceutical composition of claim 11, wherein the pharmaceutical composition comprises a compound or pharmaceutically acceptable salt thereof having the formula

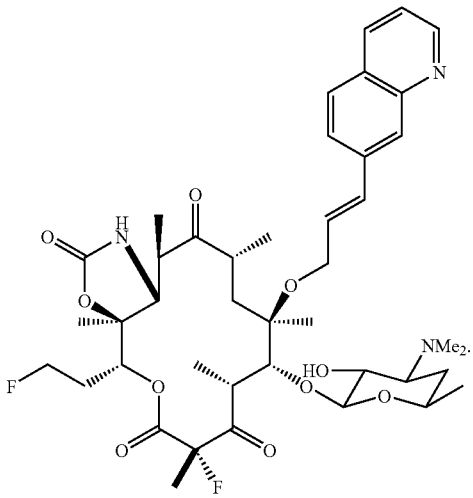

13. The pharmaceutical composition of claim 10, wherein said compound is present at between 0.05% and 5% w/w.

14. The pharmaceutical composition of claim 10, wherein the pharmaceutical composition is a liquid or solid form suitable for oral or parenteral administration.

15. A method to control bacterial infection in a subject, which method comprises administering to the subject in need of such control a therapeutically effective amount of a compound of claim 1 or pharmaceutically acceptable salt thereof or a pharmaceutical composition thereof.

16. The method of claim 15, wherein the infection is a pulmonary infection.

17. The method of claim 16, wherein the infection is selected from the group consisting of pneumonia, bronchitis, bronchiolitis, tonsillitis, and pharyngitis.

18. The method of claim 15, wherein the infection is an infection of the skin.

19. The method of claim 18, wherein the infection is acne.

20. The method of claim 15, wherein the method comprises topical administration.

21. A method of preparing a compound of formula

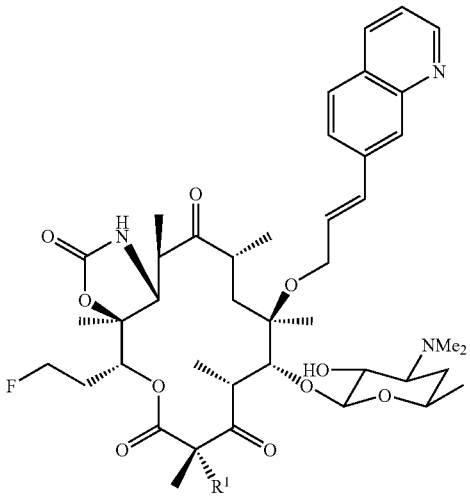

wherein $R_1$ H or F, said method comprising the steps of
(a) reacting 15-fluoroerythromycin with hydroxylamine in the presence of an acid catalyst to form 15-fluoroerythromycin 9-oxime;
(b) protecting the hydroxyl groups of 15-fluoroerythromycin 9-oxime to give 15-fluoroerythromycin 9-oxime 2',4",9-tri-O-benzoate;
(c) reacting 15-fluoroerythromycin 9-oxime 2',4",9-tri-O-benzoate with an allylating reagent to provide 6-O-allyl-15-fluoroerythromycin 9-oxime 2',4",9-tri-O-benzoate;
(d) deprotecting 6-O-allyl-15-fluoroerythromycin 9-oxime 2',4",9-tri-O-benzoate with alkali in an alcoholic solvent to give 6-O-allyl-15-fluoroerythromycin 9-oxime 2',4"-di-O-benzoate;
(e) removal of the oxime of 6-O-allyl-15-fluoroerythromycin 9-oxime 2',4"-di-O-benzoate to afford 6-O-allyl-15-fluoroerythromycin 2',4"-di-O-benzoate;
(f) reacting 6-O-allyl-15-fluoroerythromycin 2',4"-di-O-benzoate with a carbonylating reagent to obtain 6-O-allyl-11-amino-11-deoxy-15-fluoroerythromycin 11,12-cyclic carbamate 2',4"-di-O-benzoate;
(g) treating 6-O-allyl-11-amino-11-deoxy-15-fluoroerythromycin 11,12-cyclic carbamate 2',4"-di-O-benzoate with an arylating reagent under Heck coupling conditions to produce 6-O-(1-(7-quinolyl)-3-propenyl)-11-amino-11-deoxy-15-fluoroerythromycin 11,12-cyclic carbamate 2',4"-di-O-benzoate;
(h) reacting 6-O-(1-(7-quinolyl)-3-propenyl)-11-amino-11-deoxy-15-fluoroerythromycin 11,12-cyclic carbamate 2',4"-di-O-benzoate with an acid to form 6-O-(1-(7-quinolyl)-3-propenyb-11-amino-11-deoxy-3-(decladinosyl)-15-fluoroerythromycin 11,12-cyclic carbamate 2'-O-benzoate;
(i) oxidizing 6-O-(1-(7-quinolyl)-3-propenyl)-11-amino-11-deoxy-3-(decladinosyl)-15-fluoroerythromycin 11,12-cyclic carbamate 2'-O-benzoate to provide 6-O-(1-(7-quinoly)-3-propenyl)-11-amino-11-deoxy-3-(decladinosyl)-3-oxo-15-fluoroerythromycin 11,12-cyclic carbamate 2'-O-benzoate;

(J) optionally treating 6-O-(1-(7-quinolyl)-3-propenyl)-11-amino-11-deoxy-3-(decladinosyl)-3-oxo-15-fluoroerythromycin 11,12-cyclic earbamate 2'-O-benzoate with a strong base and a fluorinating agent to obtain 2-fluoro-6-O-(1-(7-quinolyl)-3-propenyl)-11-amino-11-deoxy-3-(decladinosyl)-3-oxo-15-fluoroerythromycin 11,12-cyclic carbamate 2'-O-benzoate;

(k) removing the 2'-O-benzoate; and (l) isolating the product.

22. The method of claim 21, wherein the 6-O-allyl-15-fluoroerythromycin 9-oxime 2',4",9-tri-O-benzoate prepared in step (c) is accomplished by reacting 15-fluoroerythromycin 9-oxime 2',4",9-tri-O-benzoate with tert-butyl allyl carbonate in the presence of a palladium catalyst having an isocyanide ligand.

23. The method of claim 21, wherein the 6-O-(1-(7-quinolyl)-3-propenyl)-11-amino-11-deoxy-3-(decladinosyl)-15-fluoroerythromycin 11,12-cyclic carbamate 2'-O-benzoate prepared in step (h) is accomplished under non-aqueous conditions by reacting 6-O-(1-(7-quinolyl)-3-propenyl)-11-amino-11-deoxy-15-fluoroerythiomycin 11,12-cyclic carbamate 2',4"-di-O-benzoate with an acid in the presence of a hydride source.

\* \* \* \* \*

UNITED STATES PATENT AND TRADEMARK OFFICE
CERTIFICATE OF CORRECTION

PATENT NO. : 7,595,300 B2  
APPLICATION NO. : 11/636206  
DATED : September 29, 2009  
INVENTOR(S) : Simon James Shaw et al.

It is certified that error appears in the above-identified patent and that said Letters Patent is hereby corrected as shown below:

In the Claims:

Column 46, line 58, Claim 7, delete "$C_3C_2O(C=O)CH_2CH_2$," and insert

-- $CH_3CH_2O(C=O)CH_2CH_2$, --.

Column 47, line 62, Claim 15, delete "phannaceutical" and insert -- pharmaceutical --.

Column 48, line 29, Claim 21, delete "$R_1$" and insert -- $R^1$ --.

Column 48, line 36, Claim 21, delete "fluoroerythrornycin" and insert

-- fluoroerythromycin --.

Column 48, lines 50 to 51, Claim 21, delete "fluoroerythrornycin" and insert -- fluoroerythromycin --.

Column 48, line 59, Claim 21, delete "propenyb" and insert -- propenyl) --.

Column 48, line 60, Claim 21, delete "fluoroerythrornyein" and insert

-- fluoroerythromycin --.

Column 48, line 63, Claim 21, delete "fluoroerythromyein" and insert

-- fluoroerythromycin --.

Column 48, line 65, Claim 21, delete "quinoly" and insert -- quinolyl --.

Column 49, line 3, Claim 21, delete "earbamate" and insert -- carbamate --.

Signed and Sealed this

Eighteenth Day of May, 2010

David J. Kappos  
*Director of the United States Patent and Trademark Office*

Column 50, line 9, Claim 23, delete "fluoroerythiomycin" and insert -- fluoroerythromycin --.